(12) United States Patent
Kallus et al.

(10) Patent No.: US 8,710,232 B2
(45) Date of Patent: Apr. 29, 2014

(54) IMIDAZOLE DERIVATIVES USED AS TAFIA INHIBITORS

(75) Inventors: Christopher Kallus, Frankfurt (DE); Holger Heitsch, Mainz-Kastel (DE); Andreas Lindenschmidt, Bad Soden (DE); Sven Grueneberg, Kelkheim (DE); Hauke Szillat, Frankfurt (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 1844 days.

(21) Appl. No.: 11/551,975

(22) Filed: Oct. 23, 2006

(65) Prior Publication Data

US 2007/0129341 A1 Jun. 7, 2007

Related U.S. Application Data

(63) Continuation of application No. PCT/EP2005/003630, filed on Apr. 7, 2005.

(60) Provisional application No. 60/606,782, filed on Sep. 2, 2004.

(30) Foreign Application Priority Data

Apr. 22, 2004 (DE) .......................... 10 2004 020 186

(51) Int. Cl.
  *C07D 401/12* (2006.01)
(52) U.S. Cl.
  USPC ...................................................... 546/275.1
(58) Field of Classification Search
  USPC ........................................ 546/275.1; 514/341
  See application file for complete search history.

(56) References Cited

U.S. PATENT DOCUMENTS

| | | |
|---|---|---|
| 2002/0183324 A1 | 12/2002 | Jacobson et al. |
| 2003/0083269 A1 | 5/2003 | Brouillette et al. |
| 2003/0199523 A1 | 10/2003 | Snutch |

FOREIGN PATENT DOCUMENTS

| | | |
|---|---|---|
| EP | 0 405 602 A1 | 1/1991 |
| WO | WO95/35283 | 12/1995 |
| WO | WO99/30709 | 6/1999 |
| WO | WO99/36422 | 7/1999 |
| WO | WO02/00651 A2 | 1/2002 |
| WO | WO02/00651 A3 | 1/2002 |
| WO | WO03/013526 | 2/2003 |
| WO | WO03/061653 | 7/2003 |
| WO | WO03/091211 | 11/2003 |

OTHER PUBLICATIONS

Bajzar, L, Thrombin Activatable Fibrinolysis Inhibitor and an Antifibrinolytic Pathway, Arterioscler Thromb Vasc Biol., vol. 20, (2000), pp. 2511-2518.
Barrow, J., et al., Synthesis and Evaluation of Imidazole Acetic Acid Inhibitors of Activated Thrombin-Activatable Fibrinolysis Inhibitor As Novel Antithrombotics, J. Med. Chem. 2003, 46, 5294-5297.
Bouma, B., et al., Thrombin-Activatable Fibrinolysis Inhibitor (TAFI, Plasma Procarboxypeptidase B, Procarboxypeptidase R, Procarboxypeptidase U, Journal of Thrombosis and Haemostasis (2003), 1, 1566-1574.
Nantermet, P., et al., Imidazole Acetic Acid TAFIa Inhibitors: SAR Studies Centered Around the Basic P1 Group, Bioorganic & Medicinal Chemistry Letters 14 (2004) 2141-2145.

*Primary Examiner* — Patricia L Morris
(74) *Attorney, Agent, or Firm* — Scully, Scott, Murphy & Presser, P.C.

(57) ABSTRACT

The present invention relates to compounds of formula (I)

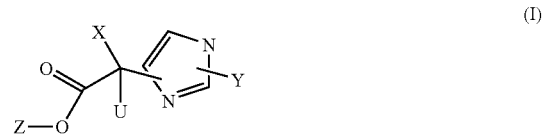

(I)

which are inhibitors of the activated thrombin-activatable fibrinolysis inhibitor. The compounds of formula (I) are suited for producing medicaments for the prevention and treatment of diseases accompanied by thromboses, embolisms, hypercoagulability or fibrotic changes.

1 Claim, No Drawings

IMIDAZOLE DERIVATIVES USED AS TAFIA INHIBITORS

CROSS REFERENCE TO RELATED APPLICATIONS

This application claims the benefit of priority from International Application No. PCT/EP2005/003630 filed on Apr. 7, 2005 from which the present application is a continuation, which claims the benefit of priority from U.S. Provisional Application No. 60/606,782, filed on Sep. 2, 2004.

FIELD OF INVENTION

The invention relates to a novel compound of the formula I which inhibits the enzyme TAFIa (activated thrombin-activatable fibrinolysis inhibitor), and to a process for its preparation and to the use thereof as a prophylactic, or for therapeutic use in humans suffering from disorders associated with thromboses, embolisms, hypercoagulability or fibrotic changes. They are suitable both for acute and for long-term therapy.

DETAILED DESCRIPTION OF THE INVENTION

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxypeptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin fragments. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects.

In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

Inhibitors of TAFIa have already been described in the international applications WO03/013526 and WO03/061653.

The invention relates to a compound of the formula I

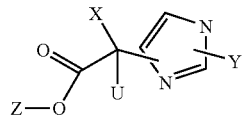

(I)

and/or all stereoisomeric forms of the compound of the formula I and/or mixtures of these forms in any ratio, and/or a physiologically tolerated salt of the compound of the formula I, where U is 1) hydrogen atom,
2) —($C_1$-$C_6$)-alkyl,
3) —($C_3$-$C_6$)-cycloalkyl,
4) fluorine,
5) —O—$CF_3$ or
6) —$CF_3$, X is the radical of the formula II

-(A1)$_m$-A2     (II)

in which
m is the integer zero or 1,
A1 is 1) —($CH_2$)$_n$— in which n is the integer 1, 2 or 3, or
2) —O—($CH_2$)$_n$— in which n is the integer zero, 1, 2 or 3,
A2 is 1) 4- to 15-membered Het ring in which Het ring comprises at least one N atom and is substituted by an amino group and may additionally be substituted independently of one another once, twice or three times by a —($C_1$-$C_3$)-alkyl, halogen, —$CF_3$ or —O—$CF_3$,
2) —($C_1$-$C_6$)-alkyl-$NH_2$ or
3) —($C_3$-$C_8$)-cycloalkyl-$NH_2$, Y is 1) the radical of the formula III

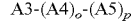

A3-(A4)$_o$-(A5)$_p$     (III)

where
a) A3 is —($C_3$-$C_8$)-cycloalkyl or —($C_2$-$C_6$)-alkynylene, in which cycloalkyl or alkynylene is unsubstituted or substituted independently of one another once, twice or three times by —O—R10 or R1,
A4 is —N(R2)$_2$— in which R2 is as defined below, and the two R2 radicals are defined independently of one another,
A5 is absent, o is the integer zero or 1, and
R10 is a hydrogen, —($C_1$-$C_6$)-alkyl or —($C_6$-$C_{14}$)-aryl,
b) A3 is —($C_3$-$C_8$)-cycloalkyl in which cycloalkyl is unsubstituted or substituted independently of one another once, twice or three times by —O—R10 or R1,
A4 is —N(R2)-, and
A5 is a)1) —C(O)—R3,
a)2) —C(O)—N(R4)-R5,
a)3) —($SO_2$)—R6, or
a)4) —C(O)—O—R7,
o is the integer 1, and
p is the integer 1,
c) A3 is cyclic amine having 3 to 8 ring atoms in which cyclic amine is unsubstituted or substituted independently of one another once, twice or three times by R1,
A4 and A5 are as defined under b),
where A5 is bonded to the N atom of A3, o is the integer zero, and
p is the integer zero or 1, or
d) A3 is —(CH$_2$)$_q$—(C$_6$-C$_{14}$)-aryl in which aryl is unsubstituted or substituted independently of one another once, twice or three times by R1,
A4 and A5 are as defined under b),
o is the integer zero or 1, and
p is the integer 1, and
q is the integer zero, 1, 2 or 3,
e) A3 is —(CH$_2$)$_r$-Het in which Het is a 4- to 15-membered Het ring, and Het ring is unsubstituted or substituted independently of one another once, twice or three times by =O or R1,
A4 and A5 are as defined under b),
o is the integer zero or 1,
p is the integer 1 and
r is the integer zero, 1, 2 or 3,
f) A3 is —(CH$_2$)$_q$—(C$_6$-C$_{14}$)-aryl in which aryl is unsubstituted or substituted independently of one another once, twice or three times by R1,
A4 is —O—,
A5 is —(C$_6$-C$_{14}$)-aryl in which aryl is unsubstituted or substituted independently of one another once, twice or three times by R1,
o and p are the integer 1 and
q is the integer zero, 1, 2 or 3,
g) —CH(—(C$_6$-C$_{14}$)-aryl)-(C$_6$-C$_{14}$)-aryl,
where R1 is
a) —(C$_6$-C$_{14}$)-aryl, where aryl is unsubstituted or substituted independently of one another once, twice or three times by —(C$_1$-C$_6$)-alkyl, —(C$_0$-C$_4$)-alkyl-(C$_3$-C$_8$)-cycloalkyl, —CF$_3$, =O, —O—CF$_3$ or halogen,
b) 4- to 15-membered Het ring,
c) —(C$_1$-C$_6$)-alkyl,
d) —(C$_0$-C$_4$)-alkyl-(C$_3$-C$_8$)-cycloalkyl,
e) —CF$_3$,
f) —O—CF$_3$ or
g) halogen,
where R2 is
a) —(C$_6$-C$_{14}$)-aryl in which aryl is unsubstituted or substituted independently of one another once, twice or three times by R1,
b) —(C$_1$-C$_6$)-alkyl in which alkyl is unsubstituted or substituted independently of one another once, twice or three times by R1,
c) —(C$_3$-C$_8$)-cycloalkyl in which cycloalkyl is unsubstituted or substituted independently of one another once, twice or three times by R1,
d) —CF$_3$ or
e) hydrogen atom,
where R3, R6 and R7 are identical or different are independently of one another
a) —(C$_1$-C$_6$)-alkyl in which alkyl is unsubstituted or substituted independently of one another once, twice or three times by R1,
b) —(C$_6$-C$_{14}$)-aryl in which aryl is unsubstituted or substituted independently of one another once, twice or three times by R1,
c) 4- to 15-membered Het ring in which Het ring is unsubstituted or substituted independently of one another once, twice or three times by R1,
d) —(C$_3$-C$_8$)-cycloalkyl in which cycloalkyl is unsubstituted or substituted independently of one another once, twice or three times by R1, or
e) hydrogen atom,
where R4 and R5 are identical or different are independently of one another
a) —(C$_1$-C$_6$)-alkyl or —(C$_2$-C$_{10}$)-alkenyl, in which alkyl or alkenyl is unsubstituted or substituted independently of one another once, twice or three times by R1,
b) —(C$_6$-C$_{14}$)-aryl in which aryl is unsubstituted or substituted independently of one another once, twice or three times by R1,
c) 4- to 15-membered Het ring in which Het ring is unsubstituted or substituted independently of one another once, twice or three times by R1,
d) —(C$_3$-C$_8$)-cycloalkyl in which cycloalkyl is unsubstituted or substituted independently of one another once, twice or three times by R1, or
e) hydrogen atom, or
R4 and R5 form together with the nitrogen atom to which they are bonded a ring having 3 to 8 ring atoms which may, in addition to the nitrogen atom, also comprise one to two additional heteroatoms from the series oxygen, sulfur or nitrogen,
Y is 2) the radical of the formula IV,

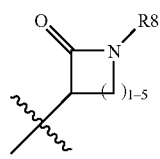

(IV)

where R8 is
a) —(C$_1$-C$_6$)-alkyl in which alkyl is unsubstituted or substituted independently of one another once, twice or three times by R1,
b) —(C$_6$-C$_{14}$)-aryl in which aryl is unsubstituted or substituted independently of one another once, twice or three times by R1,
c) 4- to 15-membered Het ring in which Het ring is unsubstituted or substituted independently of one another once, twice or three times by R1,
d) —(C$_3$-C$_8$)-cycloalkyl in which cycloalkyl is unsubstituted or substituted independently of one another once, twice or three times by R1, or
e) hydrogen atom,
Y is 3) the radical of the formula V

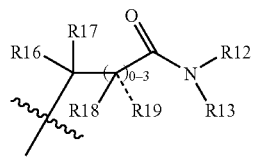

(V)

where in case a)
R12 is 1) —(C$_1$-C$_6$)-alkyl in which alkyl is unsubstituted or substituted independently of one another once, twice or three times by R1,
2) —(C$_0$-C$_3$)-alkyl-(C$_3$-C$_6$)-cycloalkyl in which cycloalkyl is unsubstituted or substituted independently of one another once, twice or three times by R1,
3) —(C$_0$-C$_3$)-alkyl-(C$_6$-C$_{14}$)-aryl in which aryl is unsubstituted or substituted independently of one another once, twice or three times by R1, or
4) —(C$_0$-C$_3$)-alkyl-Het in which Het is unsubstituted or substituted independently of one another once, twice or three times by R1, and R13 is 1) —($C_0$-$C_3$)-alkyl-($C_6$-$C_{14}$)-aryl in which alkyl and aryl are each unsubstituted or substituted independently of one another once, twice or three times by R1, or
2) —($C_0$-$C_3$)-alkyl-Het in which alkyl and Het are each unsubstituted or substituted independently of one another once, twice or three times by R1,
where in case b)
R12 is 1) hydrogen atom,
2) —($C_1$-$C_6$)-alkyl in which alkyl is unsubstituted or substituted independently of one another once, twice or three times by R1,
3) —($C_0$-$C_3$)-alkyl-($C_6$-$C_{14}$)-aryl in which aryl is unsubstituted or substituted independently of one another once, twice or three times by R1, or
4) —($C_0$-$C_3$)-alkyl-Het in which Het is unsubstituted or substituted independently of one another once, twice or three times by R1, and
R13 is —CH(R8)-R9 where R8 and R9 are independently of one another —($C_6$-$C_{14}$)-aryl or Het in which Het and aryl are each unsubstituted or substituted independently of one another once, twice or three times by —O—($C_1$-$C_4$)-alkyl or R1 and
R16, R17, R18 and R19 are identical or different and are independently of one another
1) hydrogen atom,
2) —($C_1$-$C_6$)-alkyl, in which alkyl is unsubstituted or substituted once or twice by R1,
3) halogen,
4) —OH,
5) —$NH_2$,
6) —($C_0$-$C_3$)-alkyl-($C_6$-$C_{14}$)-aryl in which alkyl and aryl are each unsubstituted or substituted independently of one another once, twice or three times by R1, or
7) —($C_0$-$C_3$)-alkyl-Het in which alkyl and Het are each unsubstituted or substituted independently of one another once, twice or three times by R1, or
R16 and R17 or R18 and R19 form together with the carbon atom to which they are respectively bonded a ring having 3 to 6 ring atoms, or
Y is 4) the radical of the formula VI,

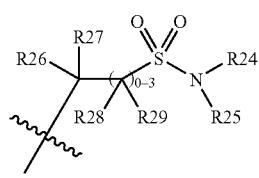

(VI)

where
R24 and R25 are identical or different and are independently of one another
1) hydrogen atom,
2) —($C_1$-$C_6$)-alkyl in which alkyl is unsubstituted or substituted once or twice by R1,
3) —($C_0$-$C_3$)-alkyl-($C_6$-$C_{14}$)-aryl in which alkyl and aryl are each unsubstituted or substituted independently of one another once, twice or three times by R1,
4) —($C_0$-$C_3$)-alkyl-Het in which alkyl and Het are each unsubstituted or substituted independently of one another once, twice or three times by R1, or
5) —($C_0$-$C_3$)-alkyl-($C_3$-$C_6$)-cycloalkyl, or
R24 and R25 form together with the nitrogen atom to which they are bonded a ring having 3 to 8 ring atoms which may, in addition to the nitrogen atom, also comprise one to two additional heteroatoms from the series oxygen, sulfur or nitrogen,
R26, R27, R28 and R29 are identical or different and are independently of one another
1) hydrogen atom,
2) —($C_1$-$C_6$)-alkyl in which alkyl is unsubstituted or substituted once or twice by R1,
3) halogen,
4) —OH,
5) —$NH_2$,
6) —($C_0$-$C_3$)-alkyl-($C_6$-$C_{14}$)-aryl in which alkyl and aryl are each unsubstituted or substituted independently of one another once, twice or three times by R1, or
7) —($C_0$-$C_3$)-alkyl-Het in which alkyl and Het are each unsubstituted or substituted independently of one another once, twice or three times by R1, or
R26 and R27 or R28 and R29 form together with the carbon atom to which they are respectively bonded a ring having 3 to 6 ring atoms,
Z is 1) hydrogen atom,
2) —($C_1$-$C_6$)-alkyl,
3) ($C_1$-$C_6$)-alkyl-OH,
4) —($C_0$-$C_4$)-alkyl-($C_3$-$C_6$)-cycloalkyl,
5) —($C_1$-$C_{10}$)-alkyl-O—C(O)—O—R1,
6) —$(CH_2)_r$—($C_6$-$C_{14}$)-aryl in which aryl is unsubstituted or substituted independently of one another once, twice or three times by R1, and r is the integer zero, 1, 2 or 3, or
7) —$(CH_2)_s$-Het in which Het is unsubstituted or substituted independently of one another once, twice or three times by R1, and s is the integer zero, 1, 2 or 3.

The invention further relates to the compound of the formula Ia

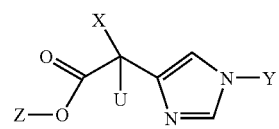

(Ia)

where

U is 1) hydrogen atom,
2) —($C_1$-$C_6$)-alkyl,
3) —($C_3$-$C_6$)-cycloalkyl,
4) fluorine,
5) —O—$CF_3$ or
6) —$CF_3$,
X is the radical of the formula II in which
m is the integer zero or 1,
A1 is 1) —$(CH_2)_n$— in which n is the integer 1, 2 or 3, or
2) —O—$(CH_2)_n$— in which n is the integer zero, 1, 2 or 3,
A2 is 1) 4- to 15-membered Het ring in which Het ring is selected from the group of acridinyl, azepinyl, azetidinyl, aziridinyl, benzimidazalinyl, benzimidazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydroisoquinolinyl, tetrahydroquinolinyl, tetrahydropyridinyl, 6H-1,2,5-thiadiazinyl, 1,2,4-thiadiazolyl, 1,2,5-thiadiazolyl, 1,3,4-thiadiazolyl, thianthrenyl, thiazolyl, thienothiazolyl, thienooxazolyl, thienoimidazolyl, thiomorpholinyl, triazinyl, 1,2,3-triazolyl, 1,2,4-triazolyl, 1,2,5-triazolyl, 1,3,4-triazolyl and xanthenyl and in which the Het ring is substituted by an amino group and may additionally be substituted independently of one another once, twice or three times by a —$(C_1-C_3)$-alkyl, halogen, —$CF_3$ or —O—$CF_3$, 2) —$(C_1-C_6)$-alkyl-$NH_2$ or
3) —$(C_3-C_8)$-cycloalkyl-$NH_2$, Y is 1) the radical of the formula III where
a) A3 is —$(C_3-C_8)$-cycloalkyl or —$(C_2-C_6)$-alkynylene in which cycloalkyl or alkylnylene is unsubstituted or substituted independently of one another once, twice or three times by R1,
A4 is —$N(R2)_2$— in which R2 is as defined below, and the two R2 radicals are defined independently of one another,
A5 is absent and
o is the integer zero or 1,
b) A3 is —$(C_3-C_8)$-cycloalkyl in which cycloalkyl is unsubstituted or substituted independently of one another once, twice or three times by R1,
A4 is —N(R2)-, and
A5 is a)1) —C(O)—R3,
a)2) —C(O)—N(R4)-R5,
a)3) —$(SO_2)$—R6, or
a)4) —C(O)—O—R7,
o is the integer 1, and
p is the integer 1,
c) A3 is cyclic amine from the group of propylamine, azetidine, pyrrolidine, piperidine, azepanes or azocanes, in which cyclic amine is unsubstituted or substituted independently of one another once, twice or three times by R1,
A4 and A5 are as defined under b),
where A5 is bonded to the N atom of A3,
o is the integer zero, and
p is the integer zero or 1, or
d) A3 is —$(CH_2)_q$—$(C_6-C_{14})$-aryl in which aryl is selected from the group of phenyl, naphthyl, anthryl or fluorenyl and is unsubstituted or substituted independently of one another once, twice or three times by R1,
A4 and A5 are as defined under b)
o is the integer zero or 1, and
p is the integer 1, and
q is the integer zero, 1, 2 or 3,
e) A3 is —$(CH_2)_r$-Het in which Het is as defined above and is unsubstituted or substituted independently of one another once, twice or three times by =O or R1,
A4 and A5 are as defined under b),
o is the integer zero or 1, p is the integer 1 and
r is the integer zero, 1, 2 or 3,
f) A3 is —$(CH_2)_q$—$(C_6-C_{14})$-aryl in which is aryl is unsubstituted or substituted independently of one another once, twice or three times by R1,
A4 is —O—,
A5 is —$(C_6-C_{14})$-aryl in which aryl is unsubstituted or substituted independently of one another once, twice or three times by R1,
o and p are the integer 1 and
q is the integer zero, 1, 2 or 3,
g) —CH(phenyl)-phenyl,
where R1 is
a) —$(C_6-C_{14})$-aryl in which aryl is as defined above and in which aryl is unsubstituted or is substituted independently of one another once, twice or three times by —$(C_1-C_6)$-alkyl, —$(C_0-C_4)$-alkyl-$(C_3-C_8)$-cycloalkyl, —$CF_3$, =O, —O—$CF_3$ or halogen
b) 4- to 15-membered Het ring in which Het is as defined above,
c) —$(C_1-C_6)$-alkyl,
d) —$(C_3-C_8)$-cycloalkyl,
e) —$CF_3$,
f) —O—$CF_3$ or
g) halogen,
where R2 is
a) —$(C_6-C_{14})$-aryl in which aryl is as defined above and is unsubstituted or substituted independently of one another once, twice or three times by R1,
b) —$(C_1-C_6)$-alkyl in which alkyl is unsubstituted or substituted independently of one another once, twice or three times by R1,
c) —$(C_3-C_8)$-cycloalkyl in which cycloalkyl is unsubstituted or substituted independently of one another once, twice or three times by R1,
d) —$CF_3$ or
e) hydrogen atom,
where R3, R6 and R7 are identical or different are independently of one another
a) —$(C_1-C_6)$-alkyl in which alkyl is unsubstituted or substituted independently of one another once, twice or three times by R1,
b) —$(C_6-C_{14})$-aryl in which aryl is as defined above and is unsubstituted or substituted independently of one another once, twice or three times by R1,
c) 4- to 15-membered Het ring in which Het ring is as defined above and is unsubstituted or substituted independently of one another once, twice or three times by R1,
d) —$(C_3-C_8)$-cycloalkyl in which cycloalkyl is unsubstituted or substituted independently of one another once, twice or three times by R1, or
e) hydrogen atom,
where R4 and R5 are identical or different are independently of one another
a) —$(C_1-C_6)$-alkyl or —$(C_2-C_{10})$-alkenyl, in which alkyl or alkenyl is unsubstituted or substituted independently of one another once, twice or three times by R1,
b) —$(C_6-C_{14})$-aryl in which aryl is as defined above and is unsubstituted or substituted independently of one another once, twice or three times by R1,
c) 4- to 15-membered Het ring in which Het ring is as defined above and is unsubstituted or substituted independently of one another once, twice or three times by R1, d) —($C_3$-$C_8$)-cycloalkyl in which cycloalkyl is unsubstituted or substituted independently of one another once, twice or three times by R1, or
e) hydrogen atom, or
R4 and R5 form together with the nitrogen atom to which they are bonded a ring having 3 to 8 ring atoms selected from the group of propylamine, azetidine, pyrrolidine, piperidine, azepanes, azocanes, azepine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, pyrazine, pyrazole, pyrazoline, pyrazolidine, pyridazine, pyridine, pyrimidine, pyrrole, pyrrolidinone, pyrroline, tetrahydropyridine, thiazole, thiadiazole, thiazolidine, thiazoline, thiomorpholine, 1,2,3-triazine, 1,2,4-triazine, 1,3,5-triazine, 1,2,3-triazole or 1,2,4-triazole, Y is 2) the radical of the formula IV where formula IV is a compound from the group of azetidin-2-one, pyrrolidin-2-one, piperidin-2-one, azepan-2-one and azocan-2-one and is substituted on the nitrogen atom in each case by R8, where R8 is
a) —($C_1$-$C_6$)-alkyl in which alkyl is unsubstituted or substituted independently of one another once, twice or three times by R1,
b) —($C_6$-$C_{14}$)-aryl in which aryl is as defined above and is unsubstituted or substituted independently of one another once, twice or three times by R1,
c) 4- to 15-membered Het ring in which Het ring is as defined above and is unsubstituted or substituted independently of one another once, twice or three times by R1,
d) —($C_3$-$C_8$)-cycloalkyl in which cycloalkyl is unsubstituted or substituted independently of one another once, twice or three times by R1, or
e) hydrogen atom, Y is 3) the radical of the formula V, where in case a)
R12 is 1) —($C_1$-$C_6$)-alkyl in which alkyl is unsubstituted or substituted independently of one another once, twice or three times by R1,
2) —($C_0$-$C_3$)-alkyl-($C_3$-$C_6$)-cycloalkyl in which cycloalkyl is unsubstituted or substituted independently of one another once, twice or three times by R1,
3) —($C_0$-$C_3$)-alkyl-($C_6$-$C_{14}$)-aryl in which aryl is as defined above and is unsubstituted or substituted independently of one another once, twice or three times by R1, or
4) —($C_0$-$C_3$)-alkyl-Het in which Het is as defined above and is unsubstituted or substituted independently of one another once, twice or three times by R1, and
R13 is 1) —($C_0$-$C_3$)-alkyl-($C_6$-$C_{14}$)-aryl in which alkyl and aryl is as defined above and are each unsubstituted or substituted independently of one another once, twice or three times by R1, or
2) —($C_0$-$C_3$)-alkyl-Het, in which alkyl and Het is as defined above and are each unsubstituted or substituted independently of one another once, twice or three times by R1, or
in case b)
R12 is 1) hydrogen atom,
2) —($C_1$-$C_6$)-alkyl in which alkyl is unsubstituted or substituted independently of one another once, twice or three times by R1,
3) —($C_0$-$C_3$)-alkyl-($C_6$-$C_{14}$)-aryl in which aryl is unsubstituted or substituted independently of one another once, twice or three times by R1, or
4) —($C_0$-$C_3$)-alkyl-Het in which Het is unsubstituted or substituted independently of one another once, twice or three times by R1, and
R13 is —CH(R8)-R9 where R8 and R9 are independently of one another —($C_6$-$C_{14}$)-aryl or Het in which Het and aryl are each as defined above and are unsubstituted or substituted independently of one another once, twice or three times by —O—($C_1$-$C_4$)-alkyl or R1, and
R16, R17, R18 and R19 are identical or different and are independently of one another
1) hydrogen atom,
2) —($C_1$-$C_6$)-alkyl in which alkyl is unsubstituted or substituted once or twice by R1,
3) halogen,
4) —OH,
5) —$NH_2$,
6) —($C_0$-$C_3$)-alkyl-($C_6$-$C_{14}$)-aryl in which alkyl and aryl is as defined above and are each unsubstituted or substituted independently of one another once, twice or three times by R1, or
7) —($C_0$-$C_3$)-alkyl-Het in which alkyl and Het is as defined above and are each unsubstituted or substituted independently of one another once, twice or three times by R1, or
R16 and R17 or R18 and R19 form together with the carbon atom to which they are respectively bonded a ring having 3 to 6 ring atoms from the group of cyclopropyl, cyclobutyl, cyclopentyl or cyclohexyl, or Y is 4) the radical of the formula VI, where
R24 and R25 are identical or different and are independently of one another
1) hydrogen atom,
2) —($C_1$-$C_6$)-alkyl in which alkyl is unsubstituted or substituted once or twice by R1,
3) —($C_0$-$C_3$)-alkyl-($C_6$-$C_{14}$)-aryl in which alkyl and aryl is as defined above and are each unsubstituted or substituted independently of one another once, twice or three times by R1,
4) —($C_0$-$C_3$)-alkyl-Het, in which alkyl and Het is as defined above and are each unsubstituted or substituted independently of one another once, twice or three times by R1, or
5) —($C_0$-$C_3$)-alkyl-($C_3$-$C_6$)-cycloalkyl, or
R24 and R25 form together with the nitrogen atom to which they are bonded a ring having 3 to 8 ring atoms from the group of propylamine, azetidine, pyrrolidine, piperidine, azepanes, azocanes, azepine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, pyrazine, pyrazole, pyrazoline, pyrazolidine, pyridazine, pyridine, pyrimidine, pyrrole, pyrrolidinone, pyrroline, tetrahydropyridine, thiazole, thiadiazole, thiazolidine, thiazoline, thiomorpholine, 1,2,3-triazine, 1,2,4-triazine, 1,3,5-triazine, 1,2,3-triazole or 1,2,4-triazole,
R26, R27, R28 and R29 are identical or different and are independently of one another
1) hydrogen atom,
2) —($C_1$-$C_6$)-alkyl in which alkyl is unsubstituted or substituted once or twice by R1,
3) halogen, 4) —OH,
5) —NH$_2$,
6) —(C$_0$-C$_3$)-alkyl-(C$_6$-C$_{14}$)-aryl in which alkyl and aryl is as defined above and are each unsubstituted or substituted independently of one another once, twice or three times by R1, or
7) —(C$_0$-C$_3$)-alkyl-Het in which alkyl and Het is as defined above and are each unsubstituted or substituted independently of one another once, twice or three times by R1, or R26 and R27 or R28 and R29 form together with the carbon atom to which they are respectively bonded a ring having 3 to 6 ring atoms from the group of cyclopropyl, cyclobutyl, cyclopentyl or cyclohexyl, Z is 1) hydrogen atom,
2) —(C$_1$-C$_6$)-alkyl,
3) (C$_3$-C$_6$)-cycloalkyl,
4) (C$_1$-C$_{10}$)-alkyl-O—C(O)—O—R1,
5) —(CH$_2$)$_r$—(C$_6$-C$_{14}$)-aryl in which aryl is as defined above and is unsubstituted or substituted independently of one another once, twice or three times by R1, and r is the integer zero, 1, 2 or 3, or
6) —(CH$_2$)$_s$-Het in which Het is as defined above and is unsubstituted or substituted independently of one another once, twice or three times by R1, and s is the integer zero, 1, 2 or 3.

The invention further relates to the compound of the formula Ia where
U is hydrogen atom, —CF$_3$, fluorine or —CH$_3$,
X is the radical of the formula II in which
  m is the integer 1,
  A1 is 1) —(CH$_2$)—,
    2) —O—(CH$_2$)$_n$— in which n is the integer zero or 1, or
    3) covalent bond,
  A2 is 1) aminopyridyl in which aminopyridyl is unsubstituted or substituted independently of one another once, twice or three times by —(C$_1$-C$_3$)-alkyl, halogen or —CH$_3$,
    2) aminothiazolyl in which aminothiazolyl is unsubstituted or substituted independently of one another once, twice or three times by —(C$_1$-C$_3$)-alkyl, halogen or —CH$_3$,
    3) —(C$_1$-C$_3$)-alkyl-NH$_2$ or
    4) —(C$_3$-C$_8$)-cycloalkyl-NH$_2$,
Y is 1) the radical of the formula III where
  a) A3 is —(C$_3$-C$_8$)-cycloalkyl or (C$_2$-C$_6$)-alkynylene in which cycloalkyl of alkynylene is unsubstituted or substituted independently of one another once, twice or three times by —O—R10 or R1,
    A4 is —N(R2)$_2$— in which R2 is as defined below, and the two R2 radicals are defined independently of one another,
    A5 is absent, o is the integer zero or 1, and
    R10 is hydrogen, —(C$_1$-C$_6$)-alkyl or phenyl,
  b) A3 is —(C$_3$-C$_6$)-cycloalkyl in which cycloalkyl is unsubstituted or substituted independently of one another once, twice or three times by —O—R10 or R1,
    A4 is —N(R2)-, and
    A5 is a)1) —C(O)—R3,
      a)2) —C(O)—N(R4)-R5,
      a)3) —(SO$_2$)—R6, or
      a)4) —C(O)—O—R7,
    o is the integer 1, and
    p is the integer 1,
  c) A3 is cyclic amine having 3 to 8 ring atoms in which cyclic amine is unsubstituted or substituted independently of one another once, twice or three times by R1,
    A4 and A5 are as defined under b),
    where R5 is bonded to the N atom of A3,
    o is the integer zero, and
    p is the integer zero or 1, or
  d) A3 is —(CH$_2$)$_q$—(C$_6$-C$_{14}$)-aryl in which aryl is unsubstituted or substituted independently of one another once, twice or three times by R1,
    A4 and A5 are as defined under b),
    o is the integer zero or 1, and
    p is the integer 1, and
    q is the integer zero, 1, 2 or 3,
  e) A3 is —(CH$_2$)$_r$-Het in which Het is pyrrolidine, benzothiophene or piperidine, which is unsubstituted or substituted independently of one another once, twice or three times by =O or R1,
    A4 and A5 are as defined under b),
    o is the integer zero or 1,
    p is the integer 1 and
    r is the integer zero, 1, 2 or 3,
  f) A3 is —(CH$_2$)$_q$-phenyl in which phenyl is unsubstituted or substituted independently of one another once, twice or three times by R1,
    A4 is —O—,
    A5 is phenyl, in which phenyl is unsubstituted or substituted independently of one another once, twice or three times by R1,
    o and p are the integer 1 and
    p is the integer 1 or 2,
where R1 is
  a) phenyl, where phenyl is unsubstituted or substituted independently of one another once, twice of three times by —(C$_1$-C$_4$)-alkyl,
  b) triazolyl or pyridinyl,
  c) —(C$_1$-C$_4$)-alkyl,
  d) —(C$_3$-C$_6$)-cycloalkyl,
  e) —CF$_3$,
  f) —O—CF$_3$,
  g) fluorine or
  h) chlorine,
where R2 is
  a) phenyl in which phenyl is unsubstituted or substituted independently of one another once, twice or three times by R1,
  b) —(C$_1$-C$_3$)-alkyl in which alkyl is unsubstituted or substituted independently of one another once, twice or three times by R1,
  c) —(C$_3$-C$_6$)-cycloalkyl in which cycloalkyl is unsubstituted or substituted independently of one another once, twice or three times by R1,
  d) —CF$_3$ or
  e) hydrogen atom,
where R3, R6 and R7 are identical or different are independently of one another
  a) —(C$_1$-C$_6$)-alkyl in which alkyl is unsubstituted or substituted independently of one another once, twice or three times by R1,
  b) —(C$_6$-C$_{14}$)-aryl in which aryl is unsubstituted or substituted independently of one another once, twice or three times by R1,
  c) 4- to 15-membered Het ring in which Het ring is unsubstituted or substituted independently of one another once, twice or three times by R1,
  d) —(C$_3$-C$_8$)-cycloalkyl in which cycloalkyl is unsubstituted or substituted independently of one another once, twice or three times by R1, or
  e) hydrogen atom, where R4 and R5 are identical or different are independently of one another
a) —($C_1$-$C_6$)-alkyl or —($C_2$-$C_6$)-alkenyl, in which alkyl or alkenyl is unsubstituted or substituted independently of one another once, twice or three times by R1,
b) —($C_6$-$C_{14}$)-aryl in which aryl is unsubstituted or substituted independently of one another once, twice or three times by R1,
c) 4- to 15-membered Het ring in which Het ring is unsubstituted or substituted independently of one another once, twice or three times by R1,
d) —($C_3$-$C_8$)-cycloalkyl in which cycloalkyl is unsubstituted or substituted independently of one another once, twice or three times by R1, or
e) hydrogen atom, or
R4 and R5 form together with the nitrogen atom to which they are bonded a ring derived from azetidine, pyrrolidine, piperidine, azepanes, azocanes, azepine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, pyrazine, pyrazole, pyrazoline, pyrazolidine, pyridazine, pyridine, pyrimidine, pyrrole, pyrrolidinone, pyrroline, tetrahydropyridine, thiazole, thiadiazole, thiazolidine, thiazoline, thiomorpholine, 1,2,3-triazine, 1,2,4-triazine, 1,3,5-triazine, 1,2,3-triazole or 1,2,4-triazole, Y is 2) the radical of the formula IV selected from the group of azetidin-2-one, pyrrolidin-2-one or piperidin-2-one, where the radical is substituted on the nitrogen atom in each case by R8,
where R8 is
a) —($C_1$-$C_6$)-alkyl in which alkyl is unsubstituted or substituted independently of one another once, twice or three times by R1,
b) phenyl in which phenyl is unsubstituted or substituted independently of one another once, twice or three times by R1,
c) hydrogen atom or
d) —($C_3$-$C_8$)-cycloalkyl in which cycloalkyl is unsubstituted or substituted independently of one another once, twice or three times by R1, Y is 3) the radical of the formula V where in the case a)
R12 is 1) —($C_1$-$C_6$)-alkyl in which alkyl is unsubstituted or substituted independently of one another once, twice or three times by R1,
2) -($C_0$-$C_3$)-alkyl-($C_3$-$C_6$)-cycloalkyl in which cycloalkyl is unsubstituted or substituted independently of one another once, twice or three times by R1, or
3) —($C_0$-$C_3$)-alkyl-phenyl in which phenyl is unsubstituted or substituted independently of one another once, twice or three times by R1, and
R13 is 1) —($C_0$-$C_3$)-alkyl-phenyl in which alkyl and phenyl are each unsubstituted or substituted independently of one another once, twice or three times by R1, or
2) —($C_0$-$C_3$)-alkyl-pyridyl in which alkyl and pyridyl are each unsubstituted or substituted independently of one another once, twice or three times by R1, or
in the case b)
R12 is 1) hydrogen atom,
2) —($C_1$-$C_6$)-alkyl in which alkyl is unsubstituted or substituted independently of one another once, twice or three times by R1,
3) —($C_0$-$C_3$)-alkyl-phenyl in which phenyl is unsubstituted or substituted independently of one another once, twice or three times by R1, or
4) —($C_0$-$C_3$)-alkyl-pyridyl in which alkyl and pyridyl are each unsubstituted or substituted independently of one another once, twice or three times by R1, and
R13 is —CH(R8)-R9 where R8 and R9 are independently of one another phenyl or pyridyl in which phenyl or pyridyl are each unsubstituted or substituted independently of one another once, twice or three times by —O—($C_1$-$C_4$)-alkyl or R1, and
R16, R17, R18 and R19 are identical or different and are independently of one another
1) hydrogen atom,
2) —($C_1$-$C_3$)-alkyl in which alkyl is unsubstituted or substituted once or twice by R1,
3) fluorine,
4) —OH,
5) —$NH_2$ or
6) —($C_0$-$C_3$)-alkyl-phenyl, in which alkyl and phenyl are each unsubstituted or substituted independently of one another once, twice or three times by R1, or Y is 4) the radical of the formula VI, where
R24 and R25 are identical or different and are independently of one another
1) hydrogen atom,
2) —($C_1$-$C_6$)-alkyl in which alkyl is unsubstituted or substituted once or twice by R1,
3) —($C_0$-$C_3$)-alkyl-phenyl in which alkyl and phenyl are each unsubstituted or substituted independently of one another once, twice or three times by R1, or
4) -($C_0$-$C_3$)-alkyl-($C_3$-$C_6$)-cycloalkyl, or
R26, R27, R28 and R29 are identical or different and are independently of one another
1) hydrogen atom,
2) —($C_1$-$C_3$)-alkyl in which alkyl is unsubstituted or substituted once or twice by R1,
3) fluorine,
4) —OH,
5) —$NH_2$ or
6) —($C_0$-$C_3$)-alkyl-phenyl in which alkyl and phenyl are each unsubstituted or substituted independently of one another once, twice or three times by R1, and
Z is hydrogen atom or ($C_1$-$C_4$)-alkyl.

The invention further relates to the compound of the formula Ia, where
U is hydrogen atom,
X is the radical of the formula II in which
m is the integer 1,
A1 is —($CH_2$)—,
A2 is aminopyridyl in which aminopyridyl is unsubstituted or substituted independently of one another once, twice or three times by halogen or —$CH_3$,
Y is 1) the radical of the formula III where
a) A3 is —($C_3$-$C_8$)-cycloalkyl in which cycloalkyl is unsubstituted or substituted independently of one another once, twice or three times by R1, and A4 and A5 are absent,
b) A3 is —($C_3$-$C_8$)-alkynylene in which alkynylene is unsubstituted or substituted independently of one another once, twice or three times by R1, and A4 and A5 are absent,
c) A3 is cyclic amine having 3 to 8 ring atoms in which cyclic amine is unsubstituted or substituted independently of one another once, twice or three times by R1, and A4 and A5 are absent, d) A3 is —(CH$_2$)$_q$-phenyl in which phenyl is unsubstituted or substituted independently of one another once, twice or three times by R1,
A4 is —N(R2)- in which R2 is as defined below
A5 is a)1) —C(O)—R3,
 a)2) —C(O)—N(R4)-R5,
 a)3) —(SO$_2$)—R6 or
 a)4) —C(O)—O—R7,
o is the integer 1, and
p is the integer 1, and
q is the integer zero, 1, or 2,
e) A3 is —(CH$_2$)$_r$-Het in which Het is a pyrrolidine or piperidine which is unsubstituted or substituted independently of one another once, twice or three times by R1,
A4 is absent and A5 is as defined under d), where A5 is bonded to the nitrogen atom of A3,
p is the integer 1, and
r is the integer zero, 1, 2 or 3,
f) A3 is —CH$_2$-phenyl, where phenyl is unsubstituted or substituted independently of one another once, twice or three times by R1,
A4 is —O—,
A5 is phenyl, where phenyl is unsubstituted or substituted independently of one another once, twice or three times by R1,
where R1 is
a) phenyl where phenyl is unsubstituted or substituted independently of one another once, twice or three times by —(C$_1$-C$_4$)-alkyl,
b) triazolyl or pyridinyl,
c) —(C$_1$-C$_4$)-alkyl,
d) —(C$_3$-C$_6$)-cycloalkyl,
e) —CF$_3$,
f) —O—CF$_3$,
g) fluorine or
i) chlorine,
where R2 is hydrogen atom or —(C$_1$-C$_3$)-alkyl in which is alkyl is unsubstituted or substituted independently of one another once, twice or three times by R1, where R3, R6 and R7 are identical or different are independently of one another
a) (C$_1$-C$_6$)-alkyl in which alkyl is unsubstituted or substituted independently of one another once, twice or three times by R1,
b) phenyl in which phenyl is unsubstituted or substituted independently of one another once, twice or three times by R1,
c) hydrogen atom, or
d) —(C$_3$-C$_6$)-cycloalkyl in which cycloalkyl is unsubstituted or substituted independently of one another once, twice or three times by R1,
where R4 and R5 are identical or different are independently of one another
a) (C$_1$-C$_6$)-alkyl or —(C$_2$-C$_6$)-alkenyl, in which alkyl or alkenyl is unsubstituted or substituted independently of one another once, twice or three times by R1,
b) phenyl in which phenyl is unsubstituted or substituted independently of one another once, twice or three times by R1,
c) hydrogen atom, or
d) —(C$_3$-C$_6$)-cycloalkyl in which cycloalkyl is unsubstituted or substituted independently of one another once, twice or three times by R1,
Y is 2) the radical of a pyrrolidin-2-one where the radical is substituted in each case by R8 on the nitrogen atom,
where R8 is
a) (C$_1$-C$_6$)-alkyl in which alkyl is unsubstituted or substituted independently of one another once, twice or three times by R1,
b) phenyl in which phenyl is unsubstituted or substituted independently of one another once, twice or three times by R1,
c) —(C$_3$-C$_6$)-cycloalkyl in which cycloalkyl is unsubstituted or substituted independently of one another once, twice or three times by R1,
Y is 3) the radical of the formula V where
R12 is hydrogen atom or —(C$_1$-C$_6$)-alkyl in which alkyl is unsubstituted or substituted independently of one another once, twice or three times by R1, and
R13 is —CH(R8)-R9 where R8 and R9 are independently of one another phenyl or pyridyl in which pyridyl and phenyl are each unsubstituted or substituted independently of one another once, twice or three times by R1, and
R16, R17, R18 and R19 are identical or different and are independently of one another
 1) hydrogen atom,
 2) —(C$_1$-C$_3$)-alkyl in which alkyl is unsubstituted or substituted once or twice by R1, or
 3) -(C$_0$-C$_3$)-alkyl-phenyl, in which alkyl and phenyl are each unsubstituted or substituted independently of one another once, twice or three times by R1, and
Z is
 1) hydrogen atom,
 2) —(C$_1$-C$_6$)-alkyl,
 3) —(C$_1$-C$_6$)-alkyl-OH,
 4) —(C$_0$-C$_4$)-alkyl-(C$_3$-C$_6$)-cycloalkyl,
 5) —(C$_1$-C$_{10}$)-alkyl-O—C(O)—O—(C$_3$-C$_6$)-cycloalkyl.
The invention further relates to a compound of the formula Ia where
U is hydrogen atom,
X is the radical of the formula II in which
 m is the integer 1,
 A1 is —(CH$_2$)—,
 A2 is the radical

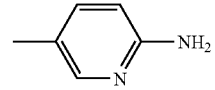

which is unsubstituted or substituted independently of one another once, twice or three times by F, Cl, Br, I or —CH$_3$,
Y is 1) the radical of the formula III where
a) A3 is —(C$_3$-C$_8$)-cycloalkyl in which cycloalkyl is unsubstituted or substituted independently of one another once, twice or three times by R1, and A4 and A5 are absent,
b) A3 is —(C$_2$-C$_4$)-alkynylene in which alkylylene is unsubstituted or substituted independently of one another once, twice or three times by R1, and A4 and A5 are absent,
c) A3 is cyclic amine having 3 to 6 ring atoms in which cyclic amine is unsubstituted or substituted independently of one another once, twice or three times by R1, and A4 and A5 are absent,
d) A3 is —(CH$_2$)$_q$-phenyl in which phenyl is unsubstituted or substituted independently of one another once, twice or three times by R1,
A4 is —N(R2)- in which R2 is as defined below, A5 is a)1) —C(O)—R3,
a)2) —C(O)—N(R4)-R5,
a)3) —(SO$_2$)—R6 or
a)4) —C(O)—O—R7,
o is the integer 1,
p is the integer 1, and
q is the integer zero, 1, or 2,
e) A3 is —(CH$_2$)$_r$-Het in which Het is a pyrrolidine or piperidine which is unsubstituted or substituted independently of one another once, twice or three times by R1,
A4 is absent and A5 is as defined under d), where A5 is bonded to the nitrogen atom of A3,
p is the integer 1, and
r is the integer zero, 1, 2 or 3,
f) A3 is —CH$_2$-phenyl, where phenyl is unsubstituted or substituted independently of one another once, twice or three times by R1,
A4 is —O—,
A5 is phenyl, where phenyl is unsubstituted or substituted independently of one another once, twice or three times by R1,
where R1 is
a) phenyl where phenyl is unsubstituted or substituted independently of one another once, twice or three times by —(C$_1$-C$_4$)-alkyl,
b) pyridyl or tetrazolyl,
c) —(C$_1$-C$_4$)-alkyl,
d) —(C$_3$-C$_6$)-cycloalkyl,
e) —CF$_3$,
f) —O—CF$_3$,
g) fluorine or
i) chlorine,
where R2 is hydrogen atom or —(C$_1$-C$_3$)-alkyl in which alkyl is unsubstituted or substituted independently of one another once, twice or three times by R1,
where R3, R6 and R7 are identical or different are independently of one another
a) —(C$_1$-C$_6$)-alkyl in which alkyl is unsubstituted or substituted independently of one another once, twice or three times by R1,
b) phenyl in which phenyl is unsubstituted or substituted independently of one another once, twice or three times by R1, or
c) —(C$_3$-C$_6$)-cycloalkyl, in which cycloalkyl is unsubstituted or substituted independently of one another once, twice or three times by R1,
where R4 and R5 are identical or different are independently of one another
a) —(C$_1$-C$_6$)-alkyl in which alkyl is unsubstituted or substituted independently of one another once, twice or three times by R1,
b) phenyl in which phenyl is unsubstituted or substituted independently of one another once, twice or three times by R1,
c) hydrogen atom, or
d) —(C$_3$-C$_8$)-cycloalkyl in which cycloalkyl is unsubstituted or substituted independently of one another once, twice or three times by R1,
Y is 2) the radical of a pyrrolidin-2-one where the radical is substituted in each case by R8 on the nitrogen atom,
where R8 is phenyl in which phenyl is unsubstituted or substituted independently of one another once, twice or three times by R1,
Y is 3) the radical of the formula V where
R12 is hydrogen atom or —(C$_1$-C$_6$)-alkyl in which alkyl is unsubstituted or substituted independently of one another once, twice or three times by R1, and
R13 is —CH(R8)-R9 where R8 and R9 are independently of one another phenyl or pyridyl in which pyridyl and phenyl are each unsubstituted or substituted independently of one another once, twice or three times by R1,
R16, R17, R18 and R19 are identical or different and are independently of one another
1) hydrogen atom,
2) —(C$_1$-C$_3$)-alkyl in which alkyl is unsubstituted or substituted once or twice by R1, or
3) -(C$_0$-C$_3$)-alkyl-phenyl, in which alkyl and phenyl are each unsubstituted or substituted independently of one another once, twice or three times by R1, and
Z is hydrogen atom.
The invention further relates to compounds of the formula Ia from the series
3-(6-Aminopyridin-3-yl)-2-(1-cyclohexyl-1H-imidazol-4-yl)propionic acid,
Methyl 3-(6-aminopyridin-3-yl)-2-(1-cyclohexyl-1H-imidazol-4-yl)propionate,
Isopropyl 3-(6-aminopyridin-3-yl)-2-(1-cyclohexyl-1H-imidazol-4-yl)propionate,
Cyclopropylmethyl 3-(6-aminopyridin-3-yl)-2-(1-cyclohexyl-1H-imidazol-4-yl)propionate,
2-Hydroxyethyl 3-(6-aminopyridin-3-yl)-2-(1-cyclohexyl-1H-imidazol-4-yl)propionate,
1-Cyclohexyloxycarbonyloxyethyl 3-(6-aminopyridin-3-yl)-2-(1-cyclohexyl-1H-imidazol-4-yl)propionate,
3-(6-Aminopyridin-3-yl)-2-(1-cyclopentyl-1H-imidazol-4-yl)propionic acid,
3-(6-Aminopyridin-3-yl)-2-(1-piperidin-4-yl-1H-imidazol-4-yl)propionic acid,
3-(6-Aminopyridin-3-yl)-2-[1-(2-oxo-1-phenylpyrrolidin-3-yl)-1H-imidazol-4-yl]propionic acid,
3-(6-Aminopyridin-3-yl)-2-{1-[(benzhydrylcarbamoyl)methyl]-1H-imidazol-4-yl}propionic acid,
Isopropyl 3-(6-aminopyridin-3-yl)-2-{1-[(benzhydrylcarbamoyl)methyl]-1H-imidazol-4-yl}propionate,
3-(6-Aminopyridin-3-yl)-2-{1-[4-(3-phenylureido)phenyl]-1H-imidazol-4-yl}propionic acid,
3-(6-Aminopyridin-3-yl)-2-{1-[2-(1-diphenylacetylpiperidin-4-yl)ethyl]-1H-imidazol-4-yl}propionic acid,
3-(6-Aminopyridin-3-yl)-2-{1-[2-(1-benzoylpiperidin-4-yl)ethyl]-1H-imidazol-4-yl}propionic acid,
3-(6-Aminopyridin-3-yl)-2-[1-(1-benzoylpiperidin-2-ylmethyl)-1H-imidazol-4-yl]propionic acid,
3-(6-Aminopyridin-3-yl)-2-(1-{2-[1-(3-phenylpropionyl)piperidin-3-yl]ethyl}-1H-imidazol-4-yl)propionic acid,
3-(6-Aminopyridin-3-yl)-2-[1-(1-diphenylacetylpiperidin-3-ylmethyl)-1H-imidazol-4-yl]-propionic acid,
3-(6-Aminopyridin-3-yl)-2-(1-{2-[1-(3-phenylpropionyl)piperidin-4-yl]ethyl}-1H-imidazol-4-yl)propionic acid,
3-(6-Aminopyridin-3-yl)-2-{1-[2-(1-phenylacetylpiperidin-3-yl)ethyl]-1H-imidazol-4-yl}-propionic acid,
3-(6-Aminopyridin-3-yl)-2-{1-[2-(1-phenylacetylpiperidin-4-yl)ethyl]-1H-imidazol-4-yl}propionic acid,
3-(6-Aminopyridin-3-yl)-2-{1-[1-(4'-methylbiphenyl-3-carbonyl)piperidin-4-ylmethyl]-1H-imidazol-4-yl}propionic acid,
3-(6-Aminopyridin-3-yl)-2-[1-(1-benzoylpiperidin-4-ylmethyl)-1H-imidazol-4-yl]propionic acid,
3-(6-Aminopyridin-3-yl)-2-(1-benzhydryl-1H-imidazol-4-yl)propionic acid, 3-(6-Aminopyridin-3-yl)-2-[1-(4-[1,2,4]triazol-1-yl-benzyl)-1H-imidazol-4-yl]propionic acid,
3-(6-Aminopyridin-3-yl)-2-[1-(4-trifluoromethoxybenzyl)-1H-imidazol-4-yl]propionic acid,
3-(6-Aminopyridin-3-yl)-2-[1-(1,1-dioxo-1H-1,6-benzo[b]thiophen-2-ylmethyl)-1H-imidazol-4-yl]propionic acid,
3-(6-Aminopyridin-3-yl)-2-[1-(5-chlorobenzo[b]thiophen-3-ylmethyl)-1H-imidazol-4-yl]-propionic acid,
3-(6-Aminopyridin-3-yl)-2-{1-[3-(4-fluorophenoxy)benzyl]-1H-imidazol-4-yl}propionic acid,
3-(6-Aminopyridin-3-yl)-2-[1-(2-phenoxybenzyl)-1H-imidazol-4-yl]propionic acid,
3-(6-Aminopyridin-3-yl)-2-[1-(4-phenoxybenzyl)-1H-imidazol-4-yl]propionic acid,
3-(6-Aminopyridin-3-yl)-2-(1-prop-2-ynyl-1H-imidazol-4-yl)propionic acid,
3-(6-Aminopyridin-3-yl)-2-(1-but-2-ynyl-1H-imidazol-4-yl)propionic acid,
3-(6-Aminopyridin-3-yl)-2-[1-(4,4-dimethylcyclohexyl)-1H-imidazol-4-yl]propionic acid,
3-(6-Aminopyridin-3-yl)-2-{1-[(benzhydrylmethylcarbamoyl)methyl]-1H-imidazol-4-yl}-propionic acid,
3-(6-Aminopyridin-3-yl)-2-[1-({[(4-chlorophenyl)phenylmethyl]carbamoyl}methyl)-1H-imidazol-4-yl]propionic acid,
3-(6-Aminopyridin-3-yl)-2-[1-({[bis-(4-methoxyphenyl)methyl]carbamoyl}methyl)-1H-imidazol-4-yl]propionic acid,
3-(6-Aminopyridin-3-yl)-2-{1-[4-(3-propylureido)phenyl]-1H-imidazol-4-yl}propionic acid,
3-(6-Aminopyridin-3-yl)-2-{1-[4-(toluene-4-sulfonylamino)phenyl]-1H-imidazol-4-yl}-propionic acid,
3-(6-Aminopyridin-3-yl)-2-{1-[3-(3-propylureido)benzyl]-1H-imidazol-4-yl}propionic acid,
3-(6-Aminopyridin-3-yl)-2-{1-[3-(3-phenethylureido)benzyl]-1H-imidazol-4-yl}propionic acid,
3-(6-Aminopyridin-3-yl)-2-{1-[3-(3-benzylureido)benzyl]-1H-imidazol-4-yl}propionic acid,
3-(6-Aminopyridin-3-yl)-2-{1-[3-(3-vinylureido)benzyl]-1H-imidazol-4-yl}propionic acid,
3-(2-Aminothiazol-4-yl)-2-{1-[(benzhydrylcarbamoyl)methyl]-1H-imidazol-4-ylpropionic acid,
3-(2-Aminothiazol-4-yl)-2-[1-({[(4-chlorophenyl)phenylmethyl]carbamoyl}methyl)-1H-imidazol-4-yl]propionic acid,
3-(6-Aminopyridin-3-yl)-2-{1-[4-(3-tert-butylureido)phenyl]-1H-imidazol-4-yl}propionic acid,
3-(6-Aminopyridin-3-yl)-2-{1-[4-(3-benzylureido)phenyl]-1H-imidazol-4-yl}propionic acid or
Ethyl 3-(6-aminopyridin-3-yl)-2-(1-cyclohexyl-1H-imidazol-4-yl)propionate.

The term "$(C_1\text{-}C_6)$-alkyl" or "$(C_1\text{-}C_{10})$-alkyl" means hydrocarbon radicals whose carbon chain is straight-chain or branched and comprises 1 to 6 carbon atoms or 1 to 10 carbon atoms, for example methyl, ethyl, propyl, isopropyl, butyl, isobutyl, tertiary butyl, pentyl, isopentyl, neopentyl, hexyl, 2,3-dimethylbutane, neohexyl, heptyl, octanyl, nonanyl or decanyl.

The term "—$(C_0\text{-}C_4)$-alkylene" means hydrocarbon radicals whose carbon chain is straight-chain or branched and comprises 1 to 4 carbon atoms, for example methylene, ethylene, propylene, isopropylene, isobutylene, butylene or tertiary butylene. "—$C_0$-alkylene" is a covalent bond.

The term "$(C_1\text{-}C_{10})$-alkyl" also means hydrocarbon radicals such as "—$(C_2\text{-}C_{10})$-alkenylene" whose carbon chain is straight-chain or branched and comprises 2 to 10 carbon atoms and have, depending on the chain length, 1, 2 or 3 double bonds, for example ethenylene, propenylene, isopropenylene, isobutenylene or butenylene; the substituents on the double bond may, if the possibility exists in principle, be arranged in the E or Z configuration.

The term "$(C_1\text{-}C_{10})$-alkyl" also means hydrocarbon radicals such as "—$(C_2\text{-}C_{10})$-alkynylene" means hydrocarbon radicals whose carbon chain is straight-chain or branched and comprises 2 to 10 carbon atoms and, depending on the chain length, have 1, 2 or 3 triple bonds, for example ethynylene, propenylene, isopropynylene, isobuthylynylene, butynylene, pentynylene or isomers of pentynylene or hexynylene or isomers of hexynylene.

The term "$(C_3\text{-}C_8)$-cycloalkyl" means radicals such as compounds derived from 3- to 8-membered monocycles such as cyclopropyl, cyclobutyl, cyclopentyl, cyclohexyl, cycloheptyl or cyclooctanyl.

The term "cyclic amine having 3 to 8 ring atoms" means radicals derived from propylamine, azetidine, pyrrolidine, piperidine, azepanes or azocanes.

The term "—$(CH_2)_n$—, —$(CH_2)_q$—, —$(CH_2)_r$— in which n, q or r is the integer zero 1, 2 or 3" means radicals such as methylene, ethylene or propylene. In the case where n, q or r is the integer zero, the radical has the meaning of a covalent bond.

The term "R16 and R17 or R18 and R19 form together with the carbon atom to which they are respectively bonded a ring having 3 to 6 ring atoms" means radicals derived from cyclopropyl, cyclobutyl, cyclopentyl or cyclohexyl.

The terms "R4 and R5 form together with the nitrogen atom to which they are bonded a ring having 3 to 8 ring atoms which may, in addition to the nitrogen atom, also comprise one to two additional heteroatoms from the series oxygen, sulfur or nitrogen" or "R24 and R25 form together with the nitrogen atom to which they are bonded a ring having 3 to 8 ring atoms which may, in addition to the nitrogen atom, also comprise one to two additional heteroatoms from the series oxygen, sulfur or nitrogen" means radicals derived from propylamine, azetidine, pyrrolidine, piperidine, azepanes, azocanes, azepine, dioxazine, 1,4-diazepane, 1,2-diazepine, 1,3-diazepine, 1,4-diazepine, imidazole, imidazoline, imidazolidine, isothiazolidine, isothiazoline, isoxazoline, isoxazolidine, 2-isoxazoline, ketopiperazine, morpholine, [1,4]oxazepane, piperazine, pyrazine, pyrazoline, pyrazolidine, pyridazine, pyrrolidinone, pyrroline, tetrahydropyridine, thiazolidine, thiazoline, thiomorpholine.

"Radicals of the formula IV" means substituents derived from azetidin-2-one, pyrrolidin-2-one, piperidin-2-one, azepan-2-one and azocan-2-one and substituted on the nitrogen atom in each case by R8.

The partial formula

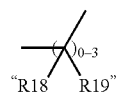

from formula V means, in the case where the branch point is present once, twice or three times, radicals such as methylene, ethylene or propylene which are in each case substituted by radicals R18 and R19. In the case where the branch point is present zero times, the result is a covalent bond.

The partial formula

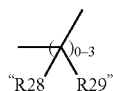

from formula VI means, in the case where the branch point is present once, twice or three times, radicals such as methylene, ethylene or propylene which are in each case substituted by radicals R28 and R29. In the case where the branch point is present zero times, the result is a covalent bond.

It should be noted in the partial formula III that the linkage to the 1H-imidazole takes place via A3 and not via A5.

The term "—$(C_6-C_{14})$-aryl" means aromatic hydrocarbon radicals having 6 to 14 carbon atoms in the ring. Examples of —$(C_6-C_{14})$-aryl radicals are phenyl, naphthyl, for example 1-naphthyl, 2-naphthyl, anthryl or fluorenyl. Naphthyl radicals and especially phenyl radicals are preferred aryl radicals.

The term "4- to 15-membered Het ring" or "Het" means ring systems having 4 to 15 carbon atoms which are present in one, two, three mutually connected ring systems and which comprise one, two or three or four identical or different heteroatoms from the series oxygen, nitrogen or sulfur. Examples of these ring systems are the radicals acridinyl, azepinyl, azetidinyl, aziridinyl, benzimidazalinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl.

Preferred Het rings are the radicals benzofuranyl, benzimidazolyl, benzoxazolyl, benzothiazolyl, benzothiophenyl, 1,3-benzodioxolyl, quinazolinyl, quinolinyl, quinoxalinyl, chromanyl, cinnolinyl, furanyl, such as 2-furanyl and 3-furanyl; imidazolyl, indolyl, indazolyl, isoquinolinyl, isochromanyl, isoindolyl, isothiazolyl, isoxazolyl, oxazolyl, phthalazinyl, pteridinyl, pyrazinyl, pyrazolyl, pyridazinyl, pyridoimidazolyl, pyridopyridinyl, pyridopyrimidinyl, pyridyl; such as 2-pyridyl, 3-pyridyl or 4-pyridyl; pyrimidinyl, pyrrolyl, such as 2-pyrrolyl and 3-pyrrolyl; purinyl, thiazolyl, tetrazolyl or thienyl; such as 2-thienyl and 3-thienyl.

The term "halogen" means fluorine, chlorine, bromine or iodine.

The term "=O" means an oxo radical or a carbonyl (—C(O)—) or nitroso radical (—N=O).

The compounds of the invention can be prepared by well-known processes or by processes described herein. Functional groups on the intermediates used, for example amino or carboxyl groups, can in this connection be masked by suitable protective groups. Examples of suitable protective groups for amino functions are the t-butoxycarbonyl, the benzyloxycarbonyl or the phthaloyl group, and the trityl or tosyl protective group. Examples of suitable protective groups for the carboxyl function are alkyl, aryl or arylalkyl esters. Protective groups can be introduced and removed by techniques which are well known or described herein (see Green, T. W., Wutz, P. G. M., *Protective Groups in Organic Synthesis* (1991), 2nd Ed., Wiley-Interscience, or Kocienski, P., *Protecting Groups* (1994), Thieme). The term protective group may also include corresponding polymer-bound protective groups. Compounds of formula (Ia) which are masked in this way, and in which the functional groups of the radical X where appropriate may likewise be masked, may, although not themselves pharmacologically active where appropriate, be converted, where appropriate after administration in mammals, by metabolism to the pharmacologically active compounds of the invention.

The invention further relates to a process for preparing the compound of the formula I and/or a stereoisomeric form of the compound of the formula I and/or a physiologically tolerated salt of the compound of the formula I, which comprises a) preparing the compound of the formula I as shown in scheme 1, where X and Y have in each case the meanings indicated above:

Scheme 1

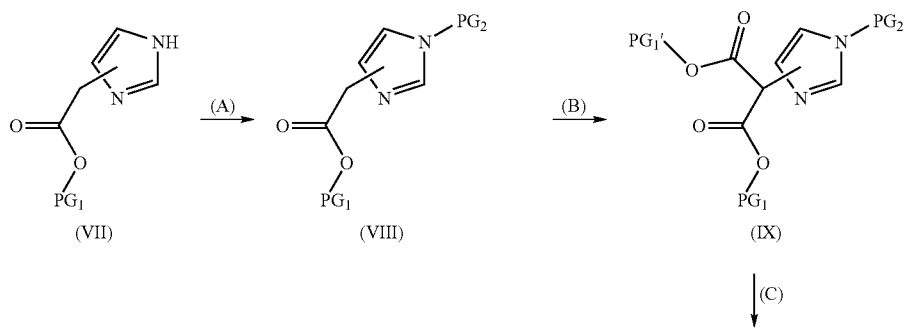

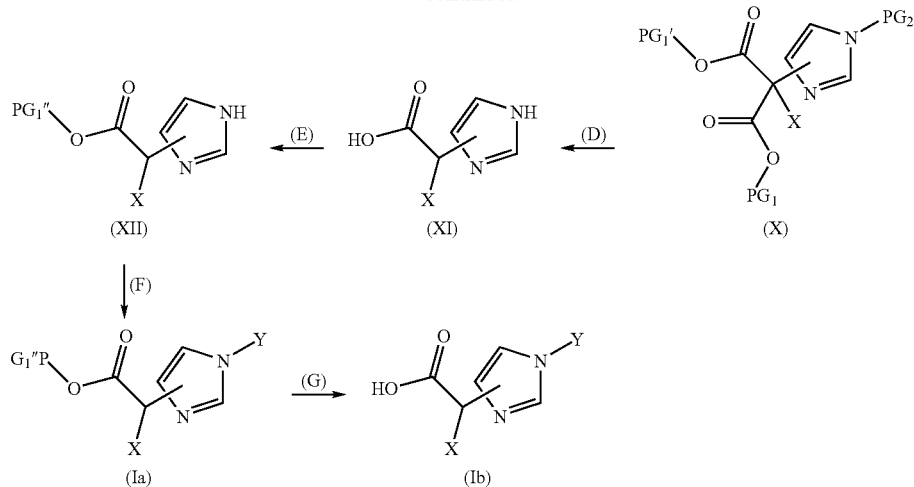

The compounds according to (VII) can be obtained by conventional methods, for example from 4-imidazoleacetic acid hydrochloride by reaction in lower alcohols in the presence of thionyl chloride, where PG1 is a suitable carboxyl protective group.

A suitable protective group PG2 is introduced by standard processes in a step (A) of the process.

The resulting compounds (VIII) are reacted in step (B) of the process in the presence of a base in an inert solvent at temperatures of between −90° C. and 50° C. with a compound of the formula

to give the compounds (IX), where PG1' is a suitable carboxyl protective group. Reaction of the compounds (IX) in step (C) of the process in the presence of a strong base in an inert solvent at temperatures between −90° C. and +50° C. with compounds of the formula

X-LG (XIV)

results in the compounds (X), where functional groups present in X may be masked by suitable protective groups and LG is a suitable activating group such as, for example, chlorine, bromine, iodine, mesylate, tosylate or triflate.

In step (D) of the process, the compounds (X) are converted into the compounds (XI) by removing the protective groups PG1, PG1' and PG2 and, where appropriate, the protective group present in X by standard processes and, where appropriate, treating under aqueous-acidic conditions at temperatures between room temperature and 100° C. The compounds (XII) can be obtained from the compounds (XI) in a step (E) by introducing a suitable carboxyl protective group PG1' under standard conditions. The compounds according to (Ia) can be obtained in a step (F) by reacting the compounds (XII) in the presence of a base at temperatures between −90° C. and +60° C. in an inert solvent with compounds of the formula

Y-LG (XV), where LG is a suitable activating group such as chlorine, bromine, iodine, mesylate, tosylate or triflate, and Y has the meanings indicated above.

The compounds (Ia) can be obtained alternatively by reacting the compounds (XII) under Mitsonobu conditions with compounds of the formula

Y—OH (XVI), in which Y has the meanings indicated above.

The compounds (Ia) can be obtained alternatively by reacting the compounds (XII) in the presence of a base at temperatures between −90° C. and +60° C. in an inert solvent with six-membered 2-fluoronitroaromatic compounds or six-membered 4-fluoronitro-aromatic compounds. The nitro group is subsequently reduced to the amino group by standard processes, e.g. at room temperature in lower alcohols with hydrogen in the presence of a transition metal catalyst or in inert solvents in the presence of tin(II) chloride dihydrate, and acylated by standard process. The compounds according to (Ib) are obtained in step (G) by removing the protective group PG1'' and, where appropriate, the protective group present in X under standard conditions.

The compounds (XIII), (XIV), (XV) and (XVI) are commercially available, known from the literature or can be prepared by processes known from the literature.

The reactions can be carried out under atmospheric, elevated or reduced pressure. They are generally carried out under atmospheric pressure.

Solvents suitable for steps (B), (C) and (F) of the process are inert organic solvents. These include for example ethers such as dioxane, THF or 1,2-dimethoxyethane, hydrocarbons such as cyclohexane, benzene, toluene or xylene, nitroaromatic compounds such as nitrobenzene, carboxamides such as dimethylformamide or dimethylacetamide, alkyl sulfoxides such as dimethyl sulfoxide, aliphatic nitriles such as acetonitrile, or other solvents such as N-methylpyrrolidinone. It is likewise possible to use mixtures of the solvents mentioned.

Bases suitable for steps (B), (C) and (F) of the process are the usual inorganic and organic bases. These preferably include alkali metal and alkaline earth metal carbonates such as sodium, potassium or calcium carbonate, alkali metal hydrides such as sodium hydride, amides such as lithium bis(trimethylsilyl)amide or lithium diisopropylamide, organic amines such as pyridine, 4-N,N-dimethylaminopyridine, triethylamine, ethyldiisopropylamine, N-methylmorpholine, N-methylpiperidine, 1,5-diazabicyclo(4.3.0)non-5-ene (DBN) or 1,8-diazabicyclo(5.4.0)undec-7-ene (DBU), or organometallic compounds such as butyllithium or phenyllithium. Sodium hydride, lithium bis(trimethylsilyl)amide and triethylamine are particularly preferred.

Mitsonobu conditions generally mean the use of inert solvents in the presence of an azodicarboxylate, where appropriate in the presence of an additional reagent, preferably in a temperature range from 0° C. to room temperature under atmospheric pressure. Examples of inert solvents are halohydrocarbons such as methylene chloride, ethers such as dioxane, THF or 1,2-dimethoxyethane, hydrocarbons such as benzene, toluene or xylene, nitroaromatic compounds such as nitrobenzene, carboxamides such as dimethylformamide or dimethylacetamide, alkyl sulfoxides such as dimethyl sulfoxide, aliphatic nitriles such as acetonitrile, esters such as ethyl benzoate or other solvents such as N-methylpyrrolidinone. It is likewise possible to use mixtures of the solvents mentioned.

Examples of usual additional reagents for the Mitsonobu reaction are triphenylphosphine, diphenyl-(2-pyridyl)phosphine or (4-dimethylaminophenyl)-diphenylphosphine. Examples of azodicarboxylates are diethyl azodicarboxylate, dimethyl azodicarboxylate, diisopropyl azodicarboxylate or di-tert-butyl azodicarboxylate.

A compound of the formula I prepared as shown in scheme 1, or a suitable precursor of the formula I, which occurs owing to its chemical structure in enantiomeric forms, by salt formation with enantiopure acids or bases, chromatography on chiral stationary phases or derivatization using chiral enantiopure compounds such as amino acids, separation of the diastereomers obtained in this way, and elimination of the chiral auxiliary groups fractionates into the pure enantiomers (process b), or the compound of the formula I prepared as shown in scheme 1 either isolates in free form or, in the case where acidic or basic groups are present, converts into physiologically tolerated salts (process c).

In step b) of the process, the compound of the formula I is, if it occurs as mixture of diastereomers or enantiomers or results as mixtures thereof in the chosen synthesis, separated into the pure stereoisomers either by chromatography on an optionally chiral support material or, if the racemic compound of the formula I is able to form salts, by fractional crystallization of the diastereomeric salts formed with an optically active base or acid as aid. Chiral stationary phases suitable for thin-layer or column chromatography to separate enantiomers are, for example, modified silica gel supports (so-called Pirkle phases) and high molecular weight carbohydrates such as triacetylcellulose. It is also possible to use for analytical purposes gas chromatographic methods on chiral stationary phases after appropriate derivatization known to the skilled worker. To separate enantiomers of the racemic carboxylic acids, diastereomeric salts differing in solubility are formed using an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I containing a basic group such as an amino group with optically active acids such as (+)-camphor-10-sulfonic acid, D- and L-tartaric acid, D- and L-lactic acid and (+) and (−)-mandelic acid into the pure enantiomers. Chiral compounds containing alcohol or amine functions can also be converted with appropriately activated or, where appropriate, N-protected enantiopure amino acids into the corresponding esters or amides, or conversely chiral carboxylic acids can be converted with carboxyl-protected enantiopure amino acids into the amides or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers which are now present by crystallization or chromatography on suitable stationary phases and then eliminating the included chiral moiety by suitable methods.

A further possibility with some of the compounds of the invention is to employ diastereomerically or enantiomerically pure starting materials to prepare the framework structures. It is thus possible where appropriate also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers (or diastereomers) is carried out at an early stage of the synthesis and not at the stage of the final products. A simplification of these separations can likewise be achieved by proceeding in two or more stages.

Acidic or basic products of the compound of the formula I may be in the form of their salts or in free form. Pharmacologically acceptable salts are preferred, for example alkali metal or alkaline earth metal salts or hydrochlorides, hydrobromides, sulfates, hemisulfates, all possible phosphates, and salts of amino acids, natural bases or carboxylic acids. Physiologically tolerated salts are prepared from compounds of the formula I able to form salts, including their stereoisomeric forms, in step c) of the process in a manner known per se. The compounds of the formula I form stable alkali metal, alkaline earth metal or, where appropriate, substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. If the compounds of the formula I have basic groups, it is also possible to prepare stable acid addition salts with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or trifluoroacetic acid.

The invention also relates to medicaments characterized by an effective content of at least one compound of the formula I and/or of a physiologically tolerated salt of the compound of the formula I and/or an optionally stereoisomeric form of the compound of the formula I, together with a pharmaceutically suitable and physiologically tolerated carrier, additive and/or further active ingredients and excipients.

By reason of the pharmacological properties, the compounds of the invention are suitable for the prophylaxis and therapy of all disorders which can be treated by inhibition of TAFIa. Thus, TAFIa inhibitors are suitable both for a prophylactic and for a therapeutic use in humans. They are suitable both for an acute treatment and for a long-term therapy. TAFIa inhibitors can be employed in patients suffering from impairments of wellbeing or diseases associated with thromboses, embolisms, hypercoagulability or fibrotic changes.

These include myocardial infarction, angina pectoris and all other types of acute coronary syndrome, stroke, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. TAFIa inhibitors can additionally be employed in all procedures leading to contact of the blood with foreign surfaces such as, for example, for dialysis patients and patients with indwelling catheters. TAFIa inhibitors can be employed to reduce the risk of thrombosis after surgical procedures such as knee and hip joint operations.

TAFIa inhibitors are suitable for the treatment of patients with disseminated intravascular coagulation, sepsis and other intravascular events associated with an inflammation. TAFIa inhibitors are additionally suitable for the prophylaxis and treatment of patients with atherosclerosis, diabetes and the metabolic syndrome and its sequelae. Impairments of the hemostatic system (e.g. fibrin deposits) have been implicated in mechanisms leading to tumor growth and tumor metastasis; TAFIa inhibitors are suitable for slowing down or preventing such processes.

Further indications for the use of TAFIa inhibitors are fibrotic changes of the lung such as chronic obstructive lung disease, adult respiratory distress syndrome (ARDS) and of the eye such as fibrin deposits after eye operations. TAFIa inhibitors are also suitable for the prevention and/or treatment of scar formation.

The medicaments of the invention can be administered by oral, inhalational, rectal or transdermal administration or by subcutaneous, intraarticular, intraperitoneal or intravenous injection. Oral administration is preferred. It is possible for stents and other surfaces which come into contact with blood in the body to be coated with TAFIa inhibitors.

The invention also relates to a process for producing a medicament, which comprises making a suitable dosage form from at least one compound of the formula I with a pharmaceutically suitable and physiologically tolerated carrier and, where appropriate, further suitable active ingredients, additives or excipients.

Suitable solid or pharmaceutical formulations are, for example, granules, powder, coated tablets, tablets, (micro) capsules, suppositories, syrups, solutions, suspensions, emulsions, drops or injectable solutions, and products with protrated release of active ingredient, in the production of which normally physiologically suitable aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, where each unit comprises as active ingredient a particular dose of the compound of the invention of the formula I. In the case of solid dosage units such as tablets, capsules, coated tablets or suspensions, this dose can be up to about 1000 mg, but preferably about 50 to 300 mg, and in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

TAFIa inhibitors can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics.

EXAMPLES

Final products are normally determined by mass spectroscopic methods (FAB-, ESI-MS) and $^1$H-NMR; the main peak or two main peaks are indicated in each case. Temperatures are stated in degrees Celsius, RT means room temperature (21° C. to 24° C.). Abbreviations used are either explained or correspond to usual conventions. Unless stated otherwise, the LC-MS analyses were carried under the following conditions:

Method A: column: YMC Jsphere 33×2.1 mm, packing material 4 μm, mobile phase: $CH_3CN$+0.05% trifluoroacetic acid (TFA): $H_2O$+0.05% TFA, gradient: 5:95 (0 min) to 95:5 (3.4 min), flow rate: 1 ml/min, temperature: 30° C.;

Method B: column: YMC Jsphere ODS H80 20×2.1 mm, packing material 4 μm, mobile phase: $CH_3CN$+0.05% trifluoroacetic acid (TFA): $H_2O$+0.05% TFA, gradient: 4:96 (0 min) to 95:5 (2.0 min), flow rate: 1 ml/min, temperature: 30° C.;

Method C: column: YMC Jsphere 33×2.1 mm, packing material 4 μm, mobile phase: $CH_3CN$+0.05% trifluoroacetic acid (TFA): $H_2O$+0.05% TFA, gradient: 5:95 (0 min) to 95:5 (2.5 min), flow rate: 1.3 ml/min, temperature: 30° C.

Unless indicated otherwise, chromatographic separations were carried out on silica gel with ethyl acetate/heptane mixtures as mobile phase, and preparative separations on reversed phase (RP) silica gel (HPLC) with trifluoroacetic acid-containing water/acetonitrile mixtures as mobile phase.

Solvents were evaporated off usually under reduced pressure at 35° C. to 45° C.

Example 1

3-(6-Aminopyridin-3-yl)-2-(1-cyclohexyl-1H-imidazol-4-yl)propionic acid

Example 1a tert-Butyl(5-methylpyridin-2-yl)carbamate

A solution of 60.54 g (277 mmol) of di-tert-butyl dicarbonate in 50 ml of $CH_2Cl_2$ was added dropwise to a solution of 30.00 g (177 mmol) of 5-methylpyridin-2-ylamine and 3.39 g (28 mmol) of 4-dimethylaminopyridine in 150 ml of $CH_2Cl_2$. The resulting solution was stirred for 16 hours (h) at room temperature and subsequently concentrated to dryness. Purification by chromatography on silica gel afforded 15.4 g of the product as a colorless solid.

MS (ES+)=209 [M+H]$^+$

Example 1b

A solution of 14.9 g (72 mmol) of the compound from example 1a was introduced into 700 ml of $CCl_4$ and heated to boiling. Addition of a mixture of 12.8 g (72 mmol) of N-bromosuccinimide and 1.2 g (7 mmol) of 2,2'-azobis(isobutyronitrile) was followed by heating under reflux for 2.5 h. The reaction mixture was filtered hot, the filter residue was washed with CCl$_4$, and the combined filtrates were freed of solvent. The residue was recrystallized from acetonitrile, filtered off with suction, washed with acetonitrile and acetonitrile/methyl tert-butyl ether (1:1) and dried under reduced pressure. 6.94 g of the desired compound were obtained in the form of a cream-colored solid.

$^1$H-NMR (500 MHz, DMSO-d$_6$): δ=1.48 (s, 9H), 4.71 (s, 2H), 7.78 (d, 1H), 7.82 (d, 1H), 8.32 (s, 1H).

Example 1c

Methyl 4-imidazoleacetate hydrochloride 5.0 g (30.75 mmol) of 4-imidazoleacetic acid were dissolved in 50 ml of methanol and then 5.6 ml (76.87 mmol) of thionyl chloride were added. The resulting solution was heated under reflux for 4 h and, after cooling, evaporated to dryness. Drying under reduced pressure afforded 5.3 g of the desired product in the form of a pale yellow solid.

MS (ES+)=141 [M+H]$^+$

Example 1d

Methyl[1-(tolyl-4-sulfonyl)-1H-imidazol-4-yl]acetate

A solution of 5.0 g (28.31 mmol) of the compound from example 1c and 9.8 ml of triethylamine (70.72 mmol) in 350 ml of CH$_2$Cl$_2$ was cooled to 0° C., and then 7.04 g (36.90 mmol) of p-toluenesulfonyl chloride were added. The solution was stirred at 0° C. for 15 minutes (min) and at room temperature (RT) for 15 min, concentrated and then washed with an ammonium chloride solution and water. The organic phase was dried over Na$_2$SO$_4$ and, after filtration, evaporated to dryness. Purification by chromatography on silica gel afforded 7.2 g of the desired product.

R$_t$ (method A)=1.71 min MS (ES+)=295 [M+H]$^+$

Example 1e

Dimethyl 2-[1-(tolyl-4-sulfonyl)-1H-imidazol-4-yl]malonate

A solution of 3.0 g (10.19 mmol) of the compound from example 1d in 50 ml of absolute tetrahydrofuran (THF) was cooled to 0° C. and 9.3 ml (11.1 mmol) of a 20% strength solution of lithium bis(trimethylsilyl)amide in THF were slowly added dropwise. After stirring at 0° C. for 30 min, 0.89 ml of methyl cyanoformate was added, and the resulting solution was slowly warmed to RT over a period of 1.5 h. The reaction solution was then poured into about 300 ml of a saturated ammonium chloride solution. It was extracted several times with ethyl acetate (EA), and the combined EA extracts were washed with water and dried over Na$_2$SO$_4$ and then evaporated to dryness. Purification by chromatography on silica gel afforded 2.2 g of the title compound.

R$_t$ (method A)=1.89 min MS (ES+)=353 [M+H]$^+$

Example 1f

Dimethyl 2-(6-tert-butyloxycarbonylaminopyridin-3-ylmethyl)-2-[1-(tolyl-4-sulfonyl-1H-imidazol-4-yl] malonate A solution of 2.2 g (6.24 mmol) of the compound from example 1e in 40 ml of absolute N,N'-dimethylformamide (DMF) was cooled to 0° C. and 150 mg (6.26 mmol) of NaH (50%) were added, and the mixture was stirred at RT for 1 h. After cooling to 0° C., 1.8 g (6.24 mmol) of 2-(6-tert-butyloxycarbonylaminopyridin-3-yl)methyl bromide were added, and the resulting solution was stirred at 0° C. for 30 min. Then 50 ml of water were added, and the mixture was extracted several times with EA. The combined EA extracts were dried over Na$_2$SO$_4$, filtered and evaporated to dryness. Purification of the residue by chromatography on silica gel afforded 2.9 g of the desired compound.

R$_t$ (method A)=2.10 min MS (ES+)=559 [M+H]$^+$

Example 1g

Ethyl 3-(6-aminopyridin-3-yl)-2-(1H-imidazol-4-yl)propionate 400.0 mg (0.72 mmol) of the compound from example 1f were suspended in a solution of 5 ml of 37% strength hydrochloric acid and 5 ml of water. The resulting suspension was heated in a microwave at 180° C. for 20 min. The reaction solution was then concentrated, and the resulting residue was taken up in 50 ml of ethanol and again concentrated. The remaining residue was dissolved in 50 ml of ethanol and, after addition of 40 ml of an ether solution saturated with gaseous HCl, the solution was stirred for 3 h. It was evaporated to dryness, the residue was taken up in 20 ml of a mixture of EA and a saturated NaHCO$_3$ solution, and the reaction solution was extracted several times with EA. The combined EA extracts were dried over Na$_2$SO$_4$, filtered and concentrated. Purification of the residue by chromatography on silica gel afforded 134 mg of the desired compound.

R$_t$ (method A)=0.20 min MS (ES+)=261 [M+H]$^+$

Example 1h

Ethyl 3-(6-aminopyridin-3-yl)-2-(1-cyclohexyl-1H-imidazol-4-yl)propionate

Method 1:

A solution of 60.1 mg (0.23 mmol) of the compound from example 1g, 37.7 mg (0.23 mmol) of bromocyclohexane and 100 μl of triethylamine in 1 ml of absolute THF was treated in a microwave at 170° C. for 40 min. The reaction solution was then taken up in a little EA/water (1:1), and the phases were separated off, dried over Na$_2$SO$_4$, filtered and evaporated to dryness. Purification by chromatography on RP silica gel with CH$_3$CN/water/0.1% TFA as mobile phase and freeze-drying of the combined product fractions afforded 18.0 mg of the desired compound as bistrifluoroacetate in the form of an amorphous solid.

As alternative to method 1, the title compound was also prepared by method 2 described below.

Method 2:

A solution of 200.0 mg (0.77 mmol) of the compound from example 1e and 39.0 mg (0.77 mmol, 60%) NaH in 5 ml of absolute DMF was stirred at RT for 1 h and then 123.7 mg (0.77 mmol) of 3-bromocyclohexene were added. The resulting solution was stirred at RT for 1 h. Addition of 2 ml of water was followed by extraction with EA several times and drying of the combined EA extracts over MgSO$_4$. Concentration, purification of the residue by chromatography on RP silica gel with water/acetonitrile (5:95) and concentration of the required fractions resulted in 152 mg of ethyl 3-(6-aminopyridin-3-yl)-2-(1-cyclohex-2-ene-1H-imidazol-4-yl)propionate. This compound was then hydrogenated in 15 ml of methanol in the presence of Pd/activated carbon (10%) at RT for 2 h. Concentration and drying under reduced pressure resulted in 127 mg of the desired title compound in the form of an amorphous solid $R_t$ (method A)=0.89 min MS (ES+)=343 [M+H]$^+$
$^1$H-NMR (500 MHz, DMSO-d$_6$): δ=1.12 (t, 3H), 1.18 (m, 1H), 1.38 (m, 2H), 1.68, (m, 3H), 1.80 (m, 2H), 2.03 (m, 2H), 3.08 (dd, 1H), 3.15 (dd, 1H), 3.42 (q, 2H), 4.10 (dt, 1H), 4.24 (m, 1H), 6.95 (d, 1H), 7.75 (m, 3H), 8.10 (s, 2H).

Example 1i 3-(6-Aminopyridin-3-yl)-2-(1-cyclohexyl-1H-imidazol-4-yl)propionic acid hydrochloride A solution of 13.7 mg (0.03 mmol) of the compound from example 1h in 0.5 ml of water and 0.5 ml of 37% strength hydrochloric acid was treated in a microwave at 180° C. for 5 min. It was then evaporated to dryness under reduced pressure, the residue was taken up in a little water, and the solution was freeze-dried. This resulted in 8.0 mg of the title compound as bishydrochloride in the form of an amorphous solid.

$R_t$ (method A)=0.80 MS (ES+)=315 [M+H]$^+$
$^1$H-NMR (400 MHz, DMSO-d$_6$): δ=0.86 (m, 1H), 1.28 (m, 5H), 1.60 (m, 3H), 1.78 (m, 2H), 1.92 (m, 2H), 2.77 (dd, 1H), 2.95 (dd, 1H), 3.55 (dt, 1H), 3.95 (m, 1H), 5.60 (s, 2H), 6.34 (d, 1H), 7.00 (s, 1H), 7.14 (dd, 1H), 7.58 (s, 1H), 7.68 (s, 1H).

The two enantiomers of the compound of example 1g were separated by chiral phase preparative chromatography; Phase: Chiralpak ADH40, column dimensions: 250×4 mm, mobile phase: heptane:ethanol:methanol 8:1:1 plus 0.1% ammonium acetate (isocratic),
Flow rate: 1 ml/min, temperature 30° C.:
Enantiomer 1: $R_t$=6.13 min Enantiomer 2: $R_t$=46.32 min.

Example 2

Methyl 3-(6-aminopyridin-3-yl)-2-(1-cyclohexyl-1H-imidazol-4-yl)propionate 3 ml of an HCl-saturated ether solution were added to a solution of 50.0 mg (0.16 mmol) of the compound from example 1i in 8 ml of methanol and stirred at room temperature for 6 h. The solution was then concentrated to dryness, and the resulting residue was dried under high vacuum. 51 mg of the title compound resulted as bishydrochloride in the form of an amorphous solid.

$R_t$ (method A)=0.90 min MS (ES+)=329 [M+H]$^+$
$^1$H-NMR (500 MHz, DMSO-d$_6$): δ=1.20 (m, 1H), 1.37 (m, 2H), 1.65 (m, 3H), 1.82 (m, 2H), 2.0 (m, 2H), 3.10 (dd, 1H), 3.18 (dd, 1H), 3.65 (s, 3H), 4.22 (m, 2H), 6.95 (d, 1H), 7.72 (m, 3H), 8.05 (s, 2H)

The two enantiomers of the compound were separated by chiral phase preparative chromatography; phase: Chiracel OD/H-61, mobile phase: heptane:propanol:methanol 15:1:1 plus 0.1% diethylamine (isocratic), flow rate: 1 ml/min., temperature: 30° C.: Enantiomer 1: $R_t$=14.05 min. Enantiomer 2: $R_t$=17.15 min.

Example 3

Isopropyl 3-(6-aminopyridin-3-yl)-2-(1-cyclohexyl-1H-imidazol-4-yl)propionate 2 ml of an HCl-saturated ether solution were added to a solution of 38.0 mg (0.12 mmol) of the compound from example 1i in 5 ml of isopropanol and stirred at RT for 4 h. The solution was then concentrated to dryness, and the resulting residue was dried under high vacuum. 25 mg of the title compound resulted as bishydrochloride in the form of an amorphous solid.

$R_t$ (method A)=0.92 min MS (ES+)=357 [M+H]$^+$
$^1$H-NMR (500 MHz, DMSO-d$_6$): δ=1.02 (d, 6H), 1.15 (m, 3H), 1.38 (m, 2H), 1.68 (m, 3H), 1.85 (m, 1H), 2.03 (m, 1H), 3.05 (dd, 1H), 3.14 (dd, 1H), 3.78 (dt, 1H), 4.20 (m, 2H), 4.90 (m, 1H), 6.90 (m, 1H), 7.74 (m, 3H), 8.00 (m, 1H)

Example 4

Cyclopropylmethyl 3-(6-aminopyridin-3-yl)-2-(1-cyclohexyl-1H-imidazol-4-yl)propionate 1 ml of an HCl-saturated ether solution was added to a solution of 50.0 mg (0.16 mmol) of the compound from example 1i in 2 ml of cyclopropylcarbinol and stirred at room temperature for 12 h. The solution was then concentrated to dryness, and the resulting residue was dried under high vacuum. Purification by chromatography on silica gel with $CH_2Cl_2$/methanol as mobile phase afforded 29 mg of the title compound in the form of an amorphous solid.

$R_t$ (method A)=0.91 min MS (ES+)=369 [M+H]$^+$
$^1$H-NMR (500 MHz, DMSO-d$_6$): δ=0.18 (m, 2H), 0.42 (m, 2H), 0.98 (m, 1H), 1.18 (m, 1H), 1.34 (m, 2H), 1.60 (m, 3H), 1.75 (d, 2H), 1.94 (d, 2H), 2.90 (m, 2H), 3.70 (m, 1H), 3.78 (d, 2H), 3.97 (m, 1H), 5.70 (s, 2H), 6.34 (d, 1H), 7.05 (s, 1H), 7.13 (d, 1H), 7.55 (s, 1H), 7.70 (s, 1H)

Example 5

2-Hydroxyethyl 3-(6-aminopyridin-3-yl)-2-(1-cyclohexyl-1H-imidazol-4-yl)propionate 0.4 ml of an HCl-saturated ether solution was added to a solution of 50.0 mg (0.16 mmol) of the compound from example 1i in 1 ml of ethylene glycol and stirred at RT for 1 h. The solution was then concentrated to dryness, and the residue was taken up in sat. $NaHCO_3$ solution and extracted with EA several times. The combined EA extracts were dried, filtered and concentrated. The resulting residue was dried under high vacuum, resulting in 33 mg of the title compound in the form of a pale yellow oil.

$R_t$ (method A)=0.85 min MS (ES+)=359 [M+H]$^+$
$^1$H-NMR (500 MHz, DMSO-d$_6$): δ=0.85 (m, 1H), 1.15-1.35 (m, 5H), 1.60 (m, 3H), 1.78 (d, 1H), 1.95 (m, 1H), 2.90 (m, 1H), 3.48 (m, 1H), 4.00 (m, 2H), 5.68 (s, 2H), 6.32 (d, 1H), 7.05 (s, 1H), 7.13 (d, 1H), 7.55 (s, 1H), 7.65 (d, 1H)

Example 6

1-Cyclohexyloxycarbonyloxyethyl 3-(6-aminopyridin-3-yl)-2-(1-cyclohexyl-1H-imidazol-4-yl)propionate A solution of 50.0 mg (0.16 mmol) of the compound from example 1i and 39 mg (0.19 mmol) of 1-cyclohexyloxycarbonyloxy-1-ethyl chloride, 13 mg (0.08 mmol) of KI and 26 mg (0.19 mmol) of $K_2CO_3$ in 2 ml of DMF was stirred at 60° C. for 12 h. Then 5 ml of water were added and the reaction solution was extracted several times with EA. The combined EA extracts were dried, filtered and concentrated to dryness. The resulting residue was purified on silica gel with $CH_2Cl_2$/methanol as mobile phase, resulting in 32 mg of the title compound in the form of an amorphous solid.

$R_t$ (method A)=0.81 min MS (ES+)=485 [M+H]$^+$

¹H-NMR (500 MHz, DMSO-d$_6$): δ=0.86 (m, 4H), 1.20-1.40 (m, 8H), 1.63 (m, 2H), 1.70 (m, 2H), 1.95 (m, 1H), 2.90 (m, 1H), 3.45 (m, 1H), 3.52 (s, 3H), 3.70 (m, 1H), 3.94 (m, 1H), 4.13 (m, 2H), 4.52 (m, 1H), 5.68 (d, 1H), 6.30 (t, 1H), 6.55 (m, 1H), 7.00 (s, 1H), 7.13 (m, 1H), 7.72 (m, 2H).

Example 7

3-(6-Aminopyridin-3-yl)-2-(1-cyclopentyl-1H-imidazol-4-yl)propionic acid

Example 7a

Cyclopentyl(1-cyclopentyl-1H-imidazol-4-yl)acetate

Imidazole-4-acetic acid hydrochloride (5.30 g; 32.60 mmol) and cesium carbonate (31.90 g, 97.80 mmol) were introduced into absolute DMF. Cyclopentyl bromide (10.5 ml; 97.80 mmol) was added thereto. The mixture was stirred at 110° C. for 3 h and then filtered through a clarifying layer, the residue was washed with $CH_2Cl_2$ and the filtrate was concentrated under reduced pressure. The residue was taken up in EA, and the solution was washed with water and 0.5N HCl. The organic phase was dried over $Na_2SO_4$ and the solvent was then removed under reduced pressure. Purification of the crude product through a cartridge (70 g of silica gel) resulted in 2.65 g of cyclopentyl (1-cyclopentyl-1H-imidazol-4-yl)acetate.

R$_t$: (method B)=0.89 min MS (ES+)=263 [M+H]$^+$

Example 7b

Cyclopentyl methyl 2-(1-cyclopentyl-1H-imidazol-4-yl)malonate

Cyclopentyl (1-cyclopentyl-1H-imidazol-4-yl)acetate (2.00 g; 7.60 mmol) was dissolved in tetrahydrofuran (THF; 45 ml). The reaction solution was cooled to 0° C. and then lithium hexamethyldisilazane (20% in THF; 6.33 ml; 7.60 mmol) was added dropwise. The mixture was stirred at 0° C. for a further hour. Then methyl cyanoformate (0.66 ml; 8.36 mmol) was added. The mixture was stirred at 0° C. for 10 min and then at RT for 7 h. The reaction solution was then added to saturated $NH_4Cl$ solution. It was extracted with EA, and the organic phase was washed with $H_2O$ and dried over $Na_2SO_4$. The solvent was removed under reduced pressure. Purification of the crude product by column chromatography (120 g of silica gel; EtOAc/n-heptane—2/1) resulted in 0.46 g of cyclopentyl methyl 2-(1-cyclopentyl-1H-imidazol-4-yl)malonate.

R$_t$ (method B)=1.01 min MS (ES+)=321 [M+H]$^+$

Example 7c

Cyclopentyl methyl 2-(6-aminopyridin-3-ylmethyl)-2-(1-cyclopentyl-1H-imidazol-4-yl)malonate Cyclopentyl methyl 2-(1-cyclopentyl-1H-imidazol-4-yl)malonate (0.46 g; 1.44 mmol) was dissolved in absolute DMF (5 ml). At 0° C., sodium hydride (50%; 0.07 g; 1.44 mmol) was added. The mixture was stirred at RT for 1 h and then cooled again to 0° C. Then tert-butyl (5-bromomethylpyridin-2-yl)carbamate (0.41 g; 1.44 mmol) was added, and the mixture was stirred at RT for 2 h. While cooling in ice, the mixture was quenched with $H_2O$ and then extracted twice with EA. The organic phase was separated off and dried over $Na_2SO_4$, and the solvent was removed under reduced pressure. Purification of the crude product through a cartridge (50 g of silica gel) resulted in 0.31 g of cyclopentyl methyl 2-(6-aminopyridin-3-ylmethyl)-2-(1-cyclopentyl-1H-imidazol-4-yl)malonate.

R$_t$ (method C)=1.47 min MS (ES+)=527 [M+H]$^+$

Example 7d 3-(6-Aminopyridin-3-yl)-2-(1-cyclopentyl-1H-imidazol-4-yl)propionic acid Cyclopentyl methyl 2-(6-aminopyridin-3-ylmethyl)-2-(1-cyclopentyl-1H-imidazol-4-yl)malonate (0.30 g; 0.57 mmol) was dissolved in absolute ethanol (5 ml). At 0° C., ethanolic HCl was added. The reaction solution was left to stand at 10° C. for 48 h. It was then concentrated under reduced pressure and the residue was taken up in 2N HCl. It was heated in a microwave (3×4 min; 180° C.). This was followed by washing with EA, and the aqueous phase was neutralized with 1N NaOH and then freeze-dried. The residue was taken up in methanol and filtered twice through a cartridge (C18). Concentration of the filtrate under reduced pressure resulted in 0.10 g of 3-(6-aminopyridin-3-yl)-2-(1-cyclopentyl-1H-imidazol-4-yl)-propionic acid.

R$_t$ (method C)=0.64 min MS (ES+)=301 [M+H]$^+$

¹H-NMR (d$^6$-DMSO): 1.60 (m, 2H); 1.73 (m, 4H); 2.18 (m, 2H), 2.87 (ddd, 1H); 3.58 (t, 1H); 3.78 (qt, 2H); 4.45 (t, 1H); 5.52 (s, 2H); 6.29 (d, 1H); 6.95 (s, 1H); 7.11 (dd; 1H); 7.55 (s, 1H); 7.65 8 (s, 1H)

Example 8

3-(6-Aminopyridin-3-yl)-2-(1-piperidin-4-yl-1H-imidazol-4-yl)propionic acid

Example 8a

Ethyl 3-(6-aminopyridin-3-yl)-2-(1-(benzyloxycarbonyl)piperidin-4-yl-1H-imidazol-4-yl)propionate A solution of 60.1 mg (0.23 mmol) of the compound from example 1g, 68.9 mg (0.23 mol) of 4-bromo-1-benzyloxycarbonylpiperidine, 97 μl (0.69 mmol) of triethylamine in 1 ml of absolute THF was treated in a microwave at 180° C. for 2 h. The reaction solution was then mixed with 2 ml of EA/water (1:1), and the EA phase was separated off and dried over $Na_2SO_4$. Filtering, stripping off the solvent and purifying the remaining residue by chromatography on RP silica gel with $CH_3CN$/water/0.1% TFA as mobile phase afforded 33 mg of the title compound as bistrifluoroacetate.

R$_t$ (method A)=1.18 min MS (ES+)=478 [M+H]$^+$

Example 8b 3-(6-Aminopyridin-3-yl)-2-(1-piperidin-4-yl-1H-imidazol-4-yl)propionic acid bishydrochloride A solution of 17.7 mg (0.03 mmol) of the compound from example 2a in 0.5 ml of water and 0.5 ml of 37% strength hydrochloric acid was treated in a microwave at 180° C. for 5 min. It was then evaporated to dryness under reduced pressure, the residue was dissolved in a little water, and the solution was freeze-dried. This resulted in 11.0 mg of the title compound in the form of an amorphous solid.

R$_t$ (method A)=0.18 min MS (ES+)=316 [M+H]$^+$

¹H-NMR (500 MHz, DMSO-d₆): δ=1.27 (m, 2H), 2.20 (m, 4H), 2.28 (m, 2H), 3.08 (dd, 1H), 3.17 (dd, 1H), 4.15 (m, 2H), 4.52 (m, 1H), 6.85 (d, 1H), 7.52 (d, 1H), 7.75 (m, 2H).

Example 9

3-(6-Aminopyridin-3-yl)-2-[1-(2-oxo-1-phenylpyrrolidin-3-yl)-1H-imidazol-4-yl]propionic acid

Example 9a

Ethyl 3-(6-aminopyridin-3-yl)-2-[1-(2-oxo-1-phenylpyrrolidin-3-yl)-1H-imidazol-4-yl]-propionate A solution of 60.1 mg (0.23 mmol) of the compound from example 1g in 1 ml of absolute DMF was mixed with 11 mg (0.23 mmol) of sodium hydride (50%) and stirred at RT for 1 h. Then 55.5 mg (0.23 mmol) of (+/−)-3-bromo-1-phenyl-2-pyrrolidinone were added, and the mixture was stirred at RT for 45 min. The reaction solution was mixed with 1 ml of water and extracted several times with EA. The combined EA extracts were dried over Na₂SO₄, filtered and concentrated. Purification of the resulting residue by chromatography on silica gel with CH₂Cl₂/methanol (92:8 to 85:15 in 35 min) as mobile phase afforded 52.2 mg of the title compound.

$R_t$ (method A)=0.93 min MS (ES+)=420 [M+H]⁺

Example 9b 3-(6-Aminopyridin-3-yl)-2-[1-(2-oxo-1-phenylpyrrolidin-3-yl)-1H-imidazol-4-yl]propionic acid bishydrochloride A solution of 23.1 mg (0.06 mmol) of the compound from example 9a in 0.5 ml of water and 0.5 ml of 37% strength hydrochloric acid was treated in a microwave at 180° C. for 3 min. The reaction solution was taken up in ethanol and concentrated under reduced pressure several times. Freeze-drying of the residue taken up in water afforded 19.0 mg of the desired compound in the form of an amorphous solid.

$R_t$ (method A)=0.73 min MS (ES+)=392 [M+H]⁺
¹H-NMR (500 MHz, DMSO-d₆): δ=2.74 (m, 1H), 3.00 (dd, 1H), 3.12 (dd, 1H), 4.91 (m, 1H), 4.02 (m, 3H), 5.48 (dd, 1H), 6.85 (d, 1H), 7.20 (t, 1H), 7.38 (m, 2H), 7.70 (m, 5H), 7.95 (broad s, 2H).

Example 10

3-(6-Aminopyridin-3-yl)-2-{1-[(benzhydrylcarbamoyl)methyl]-1H-imidazol-4-yl}-propionic acid

Example 10a

N-Benzhydryl-2-bromoacetamide

A solution of 2.91 g (14.39 mmol) of bromoacetyl bromide in 40 ml was cooled to 0° C. and 2.1 ml (14.39 mmol) of triethylamine and 2.64 g (14.39 mmol) of benzhydrylamine were successively added. The reaction solution was then evaporated to dryness under reduced pressure, and the resulting residue was purified on silica gel with EA as mobile phase. The product crystallized from the product fractions was filtered off with suction, washed with a little cold diethyl ether and dried under reduced pressure, resulting in 0.85 g of the title compound.

MS (ES+)=305 [M+H]⁺

Example 10b

Ethyl 3-(6-aminopyridin-3-yl)-2-{1-[(benzhydrylcarbamoyl)methyl]-1H-imidazol-4-yl}propionate A solution of 60.1 mg (0.23 mmol) of the compound from example 1g in 1 ml of absolute DMF was mixed with 11 mg (0.23 mmol) of sodium hydride (50%) and stirred at RT for 1 h. Then 70.3 mg (0.23 mmol) of the compound from example 10a were added, and the mixture was stirred at RT for 1 h. The reaction solution was mixed with 1 ml of water and extracted several times with EA. The combined EA extracts were dried over Na₂SO₄, filtered and concentrated. Purification of the resulting residue by chromatography on silica gel with CH₂Cl₂/methanol (9:1) as mobile phase afforded 71.4 mg of the title compound.

$R_t$ (method A)=1.24 min MS (ES+)=484 [M+H]⁺

Example 10c 3-(6-Aminopyridin-3-yl)-2-{1-[(benzhydrylcarbamoyl)methyl]-1H-imidazol-4-yl}-propionic acid bistrifluoroacetate A solution of 14 mg (0.03 mmol) of the compound from example 10b in 1 ml of THF was mixed with 147 µl of a 1N lithium hydroxide solution and stirred at RT for 30 min. After a further addition of 100 µl of a 1N lithium hydroxide solution, it was stirred at RT overnight. The pH of the solution was then adjusted to neutral by adding 1N hydrochloric acid, and this solution was evaporated to dryness under reduced pressure. Purification of the resulting residue by preparative HPLC chromatography with (0.1% TFA)/CH₃CN (5:100) as mobile phase afforded 16 mg of the desired compound.

$R_t$ (method A)=1.13 min MS (ES+)=456 [M+H]⁺
¹H-NMR (500 MHz, DMSO-d₆): δ=2.98 (dd, 1H), 3.14 (dd, 1H), 4.08 (dd, 1H), 5.00 (s, 2H), 6.08 (d, 1H), 6.87 (d, 1H), 7.27 (m, 6H), 7.35 (m, 4H), 7.50 (broad s, 1H), 7.72 (m, 2H), 7.95 (broad s, 2H), 9.38 (d, 1H).

The two enantiomers of the compound from example 10c were separated by chiral phase preparative chromatography; phase: Chiralpak ADH40, column dimensions: 250×4 mm, mobile phase: heptane:ethanol:methanol 1:1:1 plus 0.1% ammonium acetate (isocratic), flow rate: 1 ml/min, temperature: 30° C.:

Enantiomer 1: $R_t$=3.42 min Enantiomer 2: $R_t$=12.35 min.

Example 11

Isopropyl 3-(6-aminopyridin-3-yl)-2-{1-[(benzhydrylcarbamoyl)methyl]-1H-imidazol-4-yl}-propionate 3 ml of an HCl-saturated ether solution were added to a solution of 50 mg (87.8 µmol) of the compound from example 10c in 5 ml of isopropanol and stirred at room temperature for 12 h. The solution was then concentrated to dryness, and the resulting residue was dried under high vacuum. 39 mg of the title compound resulted as bishydrochloride in the form of an amorphous solid.

$R_t$ (method A)=1.31 min MS (ES+)=498 [M+H]⁺
¹H-NMR (500 MHz, DMSO-d₆): δ=1.15 (d, 6H), 3.13 (m, 2H), 4.25 (dd, 1H), 4.92 (dt, 1H), 5.10 (s, 2H), 6.15 (d, 1H), 6.94 (d, 1H), 7.28 (m, 2H), 7.33 (m, 8H), 7.53 (s, 1H), 7.75 (m, 2H), 8.05 (broad s, 1H), 9.50 (d, 1H).

Example 12

3-(6-Aminopyridin-3-yl)-2-{1-[4-(3-phenylureido)phenyl]-1H-imidazol-4-yl}propionic acid

Example 12a

Methyl(1-trityl-1H-imidazol-4-yl)acetate

A solution of 2.78 g (19.80 mmol) of the compound from example 1c, 5.52 g (19.80 mmol) of triphenylmethyl chloride and 2.00 g (19.80 mmol) of triethylamine in 5 ml of DMF was stirred at RT overnight, then poured into 200 ml of water and stirred at RT for one hour. The precipitate which separated out was filtered off with suction. The filtrate was extracted three times with EA. The combined organic phases were dried over $Na_2SO_4$, filtered and concentrated. The yellow oil resulting from this and the precipitate were combined and chromatographed on silica gel. 4.2 g of the desired compound resulted.

$^1$H-NMR (400 MHz, $CDCl_3$): δ=3.62 (s, 2H), 3.69 (s, 3H), 6.78 (s, 1H), 7.10-7.18 (m, 6H), 7.30-7.36 (m, 9H), 7.38 (s, 1H).

Example 12b

Dimethyl 2-(1-trityl-1H-imidazol-4-yl)malonate 3.50 g (9.15 mmol) of the compound from example 12a were dissolved in 50 ml of dry THF and cooled to 0° C. 1.67 g (9.96 mmol) of lithium bis(trimethylsilyl)amide as 20% strength solution in THF were added dropwise to this solution while stirring. The resulting mixture was stirred at 0° C. for 30 min and then 0.86 g (10.07 mol) of methyl cyanoformate was added. The reaction mixture was warmed to RT and stirred for a further 2 h, then poured into 400 ml of saturated aqueous $NH_4Cl$ solution and extracted twice with EA. The combined organic phases were washed with water, dried over $Na_2SO_4$, filtered and concentrated. Chromatography of the residue on silica gel afforded 1.92 g of the title compound. Repeat chromatography of the resulting mixed fraction afforded a further 40 mg of the desired compound.

$R_t$ (method C)=2.17 min MS (ES+)=498 [M+H]$^+$ $^1$H-NMR (400 MHz, $CDCl_3$): δ=3.76 (s, 6H), 4.78 (s, 1H), 6.98 (s, 1H) 7.10-7.18 (m, 6H), 7.28-7.33 (m, 9H), 7.38 (s, 1H).

Example 12c

Dimethyl 2-(6-tert-butoxycarbonylaminopyridin-3-ylmethyl)-2-(1-trityl-1H-imidazol-4-yl)malonate 0.12 g (5.12 mmol, 50%) of sodium hydride was added to a solution of 2.25 g (5.11 mmol) of the compound from example 12b in 40 ml of dry DMF at 0° C. and stirred at this temperature for 5 min. The mixture was then allowed to reach RT, was stirred for 1 h, was again cooled to 0° C. and then 1.47 g (5.11 mmol) of the compound from example 1b were added in one portion. Stirring was continued at this temperature for 30 min, then 50 ml of water were added while cooling in ice, and the mixture was extracted three times with $CH_2Cl_2$. The combined organic phases were dried over $Na_2SO_4$, filtered and concentrated. The residue was purified by chromatography on silica gel. 3.15 g of the title compound were obtained.

$^1$H-NMR (400 MHz, $CDCl_3$): δ=1.53 (s, 9H), 3.63 (s, 2H), 3.72 (s, 6H), 7.01-7.05 (m, 2H), 7.06-7.11 (m, 6H), 7.28-7.37 (m, 10H), 7.42 (s, 1H), 7.70-7.77 (m, 2H).

Example 12d

Dimethyl 2-(6-tert-butoxycarbonylaminopyridin-3-ylmethyl)-2-(1H-imidazol-4-yl)-malonate 0.20 g (1.70 mmol, 272 µl) of triethylsilane and 1.76 g (15.46 mmol, 1.19 ml) of trifluoroacetic acid were added to a solution of 1.00 g (1.55 mmol) of the compound from example 12c in 15 ml of $CH_2Cl_2$ while cooling in ice and stirring at 0° C. After 5 h, while cooling in ice, 10 ml of water were added and the pH was adjusted to 9 with 2N NaOH. The resulting precipitate was filtered off with suction, triturated in about 20 ml of $CH_2Cl_2$, filtered off with suction and dried. 0.55 g of the desired compound was obtained.

$^1$H-NMR (400 MHz, $CDCl_3$): δ=1.49 (s, 9H), 3.58 (s, 2H), 3.77 (s, 6H), 6.99 (d, 1H), 7.06 (s, 1H), 7.21 (s, 1H), 7.60-7.69 (m, 3H).

Example 12e

Dimethyl 2-(6-tert-butoxycarbonylaminopyridin-3-ylmethyl)-2-[1-(4-nitrophenyl)-1H-imidazol-4-yl]malonate A solution of 404 mg (1.00 mmol) of the compound from example 12d in 10 ml of DMF was cooled to 0° C. and, while stirring, 80 mg (2.00 mmol, 60%) of sodium hydride were added in portions. The mixture was stirred at 0° C. for 1 h and then 423 mg (3 mmol) of 4-fluoronitrobenzene were added and stirred at RT until conversion was complete. Saturated aqueous $NaHCO_3$ solution was added to the mixture, which was extracted with EA. The organic phase was dried over $Na_2SO_4$, filtered and concentrated. The residue was purified by chromatography on silica gel. 394 mg of the title compound were obtained.

$R_t$ (method B)=1.30 min. MS (ES+)=526 [M+H]$^+$

Example 12f

Dimethyl 2-[1-(4-aminophenyl)-1H-imidazol-4-yl]-2-(6-tert-butoxycarbonylaminopyridin-3-ylmethyl)malonate 824 mg (3.66 mmol) of tin(II) chloride dihydrate were added to a solution of 384 mg (0.73 mmol) of the compound from example 12e in 10 ml of DMF and stirred at RT overnight. The solvent was then evaporated off, and the residue was partitioned between EA and sat. aqueous $NaHCO_3$ solution. The aqueous phase was extracted twice with EA. The combined organic phases were dried over $Na_2SO_4$, filtered and concentrated. 103 mg of the desired compound were obtained.

$R_t$ (method B)=0.93 min. MS (ES+)=496 [M+H]$^+$

Example 12g

Dimethyl 2-(6-tert-butoxycarbonylaminopyridin-3-ylmethyl)-2-{1-[4-(3-phenylureido)phenyl]-1H-imidazol-4-yl}malonate 50 mg (0.10 mmol) of the compound from example 12f were dissolved in 10 ml of acetonitrile. The resulting solution was cooled to 0° C., and 14 mg (0.12 mmol, 13.2 µl) of phenyl isocyanate and 20 mg (0.20 mmol, 28 µl) of triethylamine were added. The mixture was warmed to RT, and a spatula tip of 4-dimethylaminopyridine was added. The reaction mixture was left to stand overnight and then evaporated, and the residue was chromatographed on silica gel. 47 mg of the title compound were obtained.

$R_t$ (method B)=1.28 min MS (ES+)=615 [M+H]$^+$

Example 12h 3-(6-Aminopyridin-3-yl)-2-{1-[4-(3-phenylureido)phenyl]-1H-imidazol-4-yl}propanoic acid 47 mg (75 µmol) of the compound from example 12g were heated in 4 ml of 50% concentrated hydrochloric acid to 100° C. After 1.5 h, the mixture was diluted with water, and the reaction mixture was freeze-dried. Preparative HPLC of the residue afforded 19 mg of the title compound as bistrifluoroacetate.

$R_t$ (method B)=0.85 min. MS (ES+)=443 [M+H]$^+$
$^1$H-NMR (400 MHz, DMSO-d$_6$): δ=3.07 (dd, 1H), 3.20 (dd, 1H), 4.00 (m, 1H), 6.90 (d, 1H), 6.98 (t, 1H), 7.30 (t, 2H), 7.43 (d, 2H), 7.61 (m, 4H), 7.78 (s, 1H), 7.80 (dd, 2H), 7.90 (s, 2H, broad), 8.82 (s, 1H, broad), 8.98 (s, 1H), 9.16 (s, 1H).

Example 13

3-(6-Aminopyridin-3-yl)-2-{1-[2-(1-diphenylacetylpiperidin-4-yl)ethyl]-1H-imidazol-4-yl}-propionic acid

Example 13a

1-[4-(2-Hydroxyethyl)piperidin-1-yl]-2,2-diphenylethanone

2-Piperidin-4-ylethanol (1.12 g; 8.65 mmol) was introduced into dimethylformamide (DMF, 10 ml). Then hydroxybenzotriazole (HOBT, 1.46 g, 9.51 mmol), 1-ethyl-3-(3-dimethylaminopropyl)carbodiimide hydrochloride (EDC.HCl, 1.83 g; 9.51 mmol) and diphenylacetic acid (2.02 g; 9.51 mmol) were added in this sequence. N,N-diisopropyl-ethylamine (DIEA; 1.67 ml; 9.51 mmol) was then added to the reaction mixture, which was stirred at RT for 16 h. The reaction solution was concentrated under reduced pressure. The residue was taken up in EA, and the organic solution was washed successively with saturated NaHCO$_3$ solution, 2N HCl and saturated NaCl solution. The organic phase was separated off, dried over Na$_2$SO$_4$, filtered and concentrated. The 1-[4-(2-hydroxyethyl)piperidin-1-yl]-2,2-diphenylethanone (2.39 g; 8.11 mmol) obtained in this way was reacted further without further purification.

$R_t$ (method B)=1.33 min MS (ES+)=324 [M+H]$^+$

Example 13b

1-[4-(2-Bromoethyl)piperidin-1-yl]-2,2-diphenylethanone

1-[4-(2-Hydroxyethyl)piperidin-1-yl]-2,2-diphenylethanone (2.39 g; 8.11 mmol) was dissolved in dichloromethane (20 ml). At room temperature, phosphorous tribromide (1.6 ml; 8.92 mmol) was slowly added dropwise. The reaction mixture was heated under reflux for 4 h. Cooling was followed by washing with saturated NaHCO$_3$ solution, 2N HCl and saturated NaCl solution, and the organic phase was separated off and dried over Na$_2$SO$_4$. The solvent was removed under reduced pressure. Purification of the residue through a cartridge (silica gel) resulted in 1-[4-(2-bromoethyl)-piperidin-1-yl]-2,2-diphenylethanone (0.75 g; 2.13 mmol).

$R_t$ (method B)=1.79 min MS (ES+)=386 [M+H]$^+$

Example 13c

Ethyl 3-(6-aminopyridin-3-yl)-2-{1-[2-(1-diphenylacetylpiperidin-4-yl)ethyl]-1H-imidazol-4-yl}propionate Ethyl 3-(6-aminopyridin-3-yl)-2-(1H-imidazol-4-yl)propionate (100 mg; 0.38 mmol) was dissolved in absolute DMF (2 ml). Sodium hydride (50%; 19 mg; 0.38 mmol) was added, and the reaction mixture was stirred at RT for 1 h. Then 1-[4-(2-bromoethyl)piperidin-1-yl]-2,2-diphenylethanone (148 mg; 0.38 mmol) dissolved in absolute DMF (1 ml) was added. The reaction mixture was stirred at RT for 1 h and then concentrated under reduced pressure. The residue was taken up in 1N HCl and washed with dichlormethane (CH$_2$Cl$_2$; 2×). The aqueous phase was made basic with 1N NaOH and extracted with CH$_2$Cl$_2$ (3×). The combined organic phases were dried over Na$_2$SO$_4$. Removal of the solvent under reduced pressure resulted in ethyl 3-(6-aminopyridin-3-yl)-2-{1-[2-(1-diphenylacetylpiperidin-4-yl)ethyl]-1H-imidazol-4-yl}propionate (71 mg; 0.12 mmol).

$R_t$ (method B)=0.98 min MS (ES+)=566 [M+H]$^+$

Example 13d 3-(6-Aminopyridin-3-yl)-2-{1-[2-(1-diphenylacetylpiperidin-4-yl)ethyl]-1H-imidazol-4-yl}propionic acid Ethyl 3-(6-aminopyridin-3-yl)-2-{1-[2-(1-diphenylacetylpiperidin-4-yl)ethyl]-1H-imidazol-4-yl}propionate (71 mg; 0.12 mmol) was dissolved in absolute ethanol (600 µl). 1N NaOH (128 µl; 0.12 mmol) was added thereto. The reaction mixture was stirred at RT for 16 h. It was then neutralized with 1N HCl (128 µl; 0.12 mmol) and concentrated under reduced pressure. It was taken up in methanol and filtered through a C$_{18}$ column. The methanol was removed and acetonitrile was added and decanted twice, and the residue was then triturated with diethyl ether. The precipitate was filtered off and dried under high vacuum at 40° C. 3-(6-Aminopyridin-3-yl)-2-{1-[2-(1-diphenylacetylpiperidin-4-yl)ethyl]-1H-imidazol-4-yl}propionic acid (50 mg; 0.09 mmol) was obtained as a colorless solid.

$R_t$ (method C)=1.20 min MS (ES+)=538 [M+H]$^+$
$^1$H-NMR (500 MHz, d$^6$-DMSO): 0.90 (m, 1H); 1.02-1.51 (m, 5H); 1.61 (m, 2H); 2.67 (m, 2H); 2.94 (m, 1H); 3.11 (m, 1H); 3.18-3.56 (m, 3H), 3.65 (m, 1H); 3.90 (m, 1H); 4.09 (t; 1H); 5.54 (m; 2H); 6.29 (d, 1H); 6.89 (s, 1H); 7.23 (m, 12H); 7.65 (m, 1H)

Example 14

3-(6-Aminopyridin-3-yl)-2-{1-[2-(1-benzoylpiperidin-4-yl)ethyl]-1H-imidazol-4-yl}propionic acid The title compound (54 mg; 0.12 mmol) was synthesized in analogy to example 13.

$R_t$ (method C)=0.88 min MS (ES+)=448 [M+H]$^+$
$^1$H-NMR (500 MHz, d$^6$-DMSO): 1.10 (m, 2H); 1.41 (m, 1H); 1.60 (m, 3H); 1.72 (m, 1H); 2.71 (m, 2H); 2.95 (m, 2H); 3.48 (m, 3H); 3.92 (t, 2H); 4.45 (m, 1H); 5.57 (s; 2H); 6.28 (d, 1H); 6.90 (s, 1H); 7.11 (d, 1H); 7.32 (m, 2H); 7.43 (m, 3H); 7.49 (s, 1H); 7.61 (s, 1H)

Example 15

3-(6-Aminopyridin-3-yl)-2-[1-(1-benzoylpiperidin-2-ylmethyl)-1H-imidazol-4-yl]propionic acid The title compound (41 mg; 0.09 mmol) was synthesized in analogy to example 13.

$R_t$ (method C)=0.81 min MS (ES+)=434 [M+H]$^+$ $^1$H-NMR (500 MHz, d$^6$-DMSO): 1.12 (m, 2H); 1.39 (m, 1H); 1.61 (m, 1H); 1.92 (m, 1H); 2.80 (m, 4H); 3.48 (m, 5H); 4.20 (m, 1H); 5.60 (s; 2H); 6.28 (d, 1H); 6.90 (m, 1H); 7.10 (d, 1H); 7.35 (m, 6H); 7.61 (s, 1H)

Example 16

3-(6-Aminopyridin-3-yl)-2-(1-{2-[1-(3-phenylpropionyl)piperidin-3-yl]ethyl}-1H-imidazol-4-yl)propionic acid The title compound (15 mg; 0.03 mmol) was synthesized in analogy to example 13.

$R_t$ (method C)=1.04 min MS (ES+)=476 [M+H]$^+$ $^1$H-NMR (500 MHz, d$^6$-DMSO): 1.15 (m, 3H); 1.55 (m, 3H); 1.75 (m, 1H); 2.59 (m, 2H); 2.77 (m, 2H); 2.92 (m, 2H); 3.40 (m, 4H); 3.65 (m, 1H); 3.89 (t, 2H); 4.15 (m, 1H); 5.55 (s, 2H); 6.28 (d, 1H); 6.89 (m, 1H); 7.13 (m, 2H); 7.22 (m, 4H); 7.45 (s, 1H); 7.63 (m, 1H)

Example 17

3-(6-Aminopyridin-3-yl)-2-[1-(1-diphenylacetylpiperidin-3-ylmethyl)-1H-imidazol-4-yl]-propionic acid The title compound (19 mg; 0.03 mmol) was synthesized in analogy to example 13.

$R_t$ (method C)=1.13 min MS (ES+)=524 [M+H]$^+$ $^1$H-NMR (500 MHz, d$^6$-DMSO): 0.85-1.75 (m, 5H); 2.55-3.07 (m, 4H); 3.07-3.83 (m, 6H); 4.09 (m, 1H); 5.62 (m, 2H); 6.29 (m, 1H); 6.89 (m, 1H); 7.23 (m, 12H); 7.65 (m, 1H)

Example 18

3-(6-Aminopyridin-3-yl)-2-(1-{2-[1-(3-phenylpropionyl)piperidin-4-yl]ethyl}1H-imidazol-4-yl)propionic acid The title compound (81 mg; 0.17 mmol) was synthesized in analogy to example 13.

$R_t$ (method C)=1.00 min MS (ES+)=476 [M+H]$^+$ $^1$H-NMR (500 MHz, d$^6$-DMSO): 0.92 (m, 2H); 1.32 (m, 1H); 1.55 (m, 4H); 2.55 (m, 2H); 2.85 (m, 2H); 3.40 (m, 4H); 3.79 (m, 1H); 3.88 (t, 2H); 4.33 (d, 1H); 5.65 (s, 2H); 6.29 (d, 1H); 6.89 (s, 1H); 7.13 (m, 2H); 7.22 (m, 4H); 7.45 (s, 1H); 7.63 (m, 1H)

Example 19

3-(6-Aminopyridin-3-yl)-2-{1-[2-(1-phenylacetylpiperidin-3-yl)ethyl]-1H-imidazol-4-yl}-propionic acid The title compound (28 mg; 0.06 mmol) was synthesized in analogy to example 13.

$R_t$ (method C)=0.93 min MS (ES+)=462 [M+H]$^+$ $^1$H-NMR (500 MHz, d$^6$-DMSO): 0.90 (m, 2H); 1.35 (m, 1H); 1.58 (m, 4H); 2.80 (m, 2H); 2.95 (m, 2H); 3.40 (m, 4H); 3.69 (s, 1H); 3.85 (t, 2H), 4.33 (d, 1H); 5.60 (s, 2H); 6.29 (d, 1H); 6.90 (s, 1H); 7.10 (dd, 1H); 7.19 (m, 3H); 7.27 (m, 2H); 7.48 (s, 1H); 7.61 (m, 1H)

Example 20

3-(6-Aminopyridin-3-yl)-2-{1-[2-(1-phenylacetylpiperidin-4-yl)ethyl]-1H-imidazol-4-yl}-propionic acid The title compound (41 mg; 0.08 mmol) was synthesized in analogy to example 13.

$R_t$ (method C)=0.91 min MS (ES+)=462 [M+H]$^+$ $^1$H-NMR (500 MHz, d$^6$-DMSO): 0.92 (m, 2H); 1.25 (m, 1H); 1.58 (m, 4H); 2.65-4.20 (m, 12H); 5.65 (m, 2H); 6.29 (m, 1H); 6.90 (m, 1H); 7.20 (6H); 7.60 (m, 2H)

Example 21

3-(6-Aminopyridin-3-yl)-2-{1-[1-(4'-methylbiphenyl-3-carbonyl)piperidin-4-ylmethyl]-1H-imidazol-4-yl}propionic acid The title compound (33 mg; 0.06 mmol) was synthesized in analogy to example 13.

$R_t$ (method C)=1.21 min MS (ES+)=524 [M+H]$^+$ $^1$H-NMR (500 MHz, d$^6$-DMSO): 1.12 (m, 2H); 1.45 (m, 2H); 1.95 (m, 1H); 2.36 (s, 3H); 2.80-3.60 (m, 6H); 3.71 (t, 1H); 3.85 (d, 2H); 4.45 (m, 1H); 6.49 (d, 1H); 6.60 (m, 2H); 6.87 (s, 1H); 7.29 (m, 4H); 7.58 (m, 4H); 7.65 (m, 1H); 7.72 (m, 2H)

Example 22

3-(6-Aminopyridin-3-yl)-2-[1-(1-benzoylpiperidin-4-ylmethyl)-1H-imidazol-4-yl]propionic acid The title compound (46 mg; 0.10 mmol) was synthesized in analogy to example 13.

$R_t$ (method C)=0.81 min MS (ES+)=434 [M+H]$^+$ $^1$H-NMR (500 MHz, d$^6$-DMSO): 1.10 (m, 2H); 1.45 (m, 2H); 1.95 (m, 1H); 2.80-3.10 (m, 4H); 3.50 (m, 2H) 3.62 (t, 1H); 3.82 (d, 2H); 4.48 (m, 1H); 6.03 (m, 2H); 6.48 (d, 1H); 6.90 (d, 1H); 7.19 (d, 1H); 7.35 (m, 2H); 7.42 (m, 3H); 7.55 (s, 1H); 7.61 (s, 1H)

Example 23

3-(6-Aminopyridin-3-yl)-2-(1-benzhydryl-1H-imidazol-4-yl)propionic acid 11 mg (0.23 mmol, 50%) of sodium hydride were added to a solution of 50 mg (0.19 mmol) of ethyl 3-(6-aminopyridin-3-yl)-2-(1H-imidazol-4-yl)propionate (example 1g) in 0.5 ml of DMF at RT and stirred for 1 h. Then 48 mg (0.19 mmol) of bromodiphenyl-methane were added, and the mixture was stirred at RT for 3.5 h. It was then heated at 60° C. for 2 h and, after cooling, 1 ml of water was added, the mixture was extracted with EA, and the organic phase was dried over Na$_2$SO$_4$, filtered and concentrated. Chromatography on silica gel afforded ethyl 3-(6-aminopyridin-3-yl)-2-(1-benzhydryl-1H-imidazol-4-yl)propionate. The product obtained in this way was taken up in 0.4 ml of 50% concentrated hydrochloric acid and treated in a microwave at 180° C. for 3 min. Freeze-drying after cooling of the reaction mixture afforded 5 mg of the title compound as bishydrochloride.

$R_t$ (method A)=1.04 min. MS (ES+)=399 [M+H]$^+$

¹H-NMR (500 MHz, d⁶-DMSO): 3.05 (dd, 1H); 3.11 (dd, 1H); 3.70 (m, 1H); 4.12 (m, 1H); 6.38 (dd, 1H); 7.02 (s, 1H); 7.12 (dd, 1H), 7.23-7.51 (m, 6H), 7.67 (d, 1H), 7.72 (m, 1H); 8.02 (s, br, 2H), 9.03 (s, 1H).

Example 24

3-(6-Aminopyridin-3-yl)-2-[1-(4-[1,2,4]triazol-1-ylbenzyl)-1H-imidazol-4-yl]propionic acid 11 mg (0.23 mmol, 50%) of sodium hydride were added to a solution of 60 mg (0.23 mmol) of ethyl 3-(6-aminopyridin-3-yl)-2-(1H-imidazol-4-yl)propionate (example 1g) in 0.5 ml of DMF at RT, and stirred for 1 h. Then 55 mg (0.23 mmol) of 1-[4-(bromomethyl)phenyl]-1H-1,2,4-triazole were added, and the mixture was stirred at RT for 3 h. After this, 1 ml of water was added, the mixture was extracted with EA, and the organic phase was dried over $Na_2SO_4$, filtered and concentrated. Chromatography on silica gel afforded ethyl 3-(6-aminopyridin-3-yl)-2-[1-(4-[1,2,4]triazol-1-ylbenzyl)-1H-imidazol-4-yl]propionate. The product obtained in this way was taken up in 0.4 ml of 50% concentrated hydrochloric acid and treated in the microwave at 180° C. for 3 min. Freeze-drying after cooling of the reaction mixture afforded 5 mg of the title compound as bishydrochloride.

$R_t$ (method A)=0.16 min. MS (ES+)=390 [M+H]⁺
¹H-NMR (500 MHz, d⁶-DMSO): 3.03 (dd, 1H); 3.21 (dd, 1H); 4.21 (m, 1H); 5.45 (s, 2H); 6.91 (d, 1H); 7.50 (d, 2H); 7.60 (s, 1H); 7.70-7.78 (m, 2H); 7.86 (d, 1H); 7.95 (d, 2H); 8.08 (s, br, 2H); 8.26 (s, 1H); 9.28 (s, 1H), 9.38 (s, 1H).

Example 25

3-(6-Aminopyridin-3-yl)-2-[1-(4-trifluoromethoxy-benzyl)-1H-imidazol-4-yl]propionic acid The title compound was prepared in analogy to example 24.

$R_t$ (method A)=1.04 min. MS (ES+)=407 [M+H]⁺
¹H-NMR (500 MHz, d⁶-DMSO): 2.98 (dd, 1H); 3.12 (dd, 1H); 4.02 (m, 1H); 5.33 (s, 2H); 6.84 (d, 1H); 7.30 (dd, 1H); 7.35-7.46 (m, 4H); 7.68 (m, 2H); 7.93 (s, br, 2H), 8.75 (s, br, 1H).

Example 26

3-(6-Aminopyridin-3-yl)-2-[1-(1,1-dioxo-1H-1,6-benzo[b]thiophen-2-ylmethyl)-1H-imidazol-4-yl]propionic acid The title compound was prepared in analogy to example 24.

$R_t$ (method A)=0.88 min. MS (ES+)=411 [M+H]⁺
¹H-NMR (500 MHz, d⁶-DMSO): 2.10 (s, 2H); 3.06 (dd, 1H); 3.18 (dd, 1H); 3.99 (m, 1H); 7.40 (d, 1H); 7.22 (d, 1H); 7.60 (s, 1H); 7.70-7.82 (m, 5H); 7.98 (s, br, 2H); 7.99 (s, 1H); 8.46 (s, 1H).

Example 27

3-(6-Aminopyridin-3-yl)-2-[1-(5-chlorobenzo[b]thiophen-3-ylmethyl)-1H-imidazol-4-yl]-propionic acid The title compound was prepared in analogy to example 24 and was obtained as bistrifluoroacetate after preparative HPLC.

$R_t$ (method A)=0.98 min. MS (ES+)=413 [M+H]⁺
¹H-NMR (500 MHz, d⁶-DMSO): 2.98 (dd, 1H); 3.13 (dd, 1H); 4.06 (m, 1H); 5.61 (s, 2H); 6.78 (d, 1H); 7.42-7.53 (m, 2H); 7.63 (d, 1H); 7.70 (s, 1H); 7.84-7.98 (m, 3H); 8.02 (s, 1H); 8.09 (d, 1H); 8.92 (s, br, 1H).

Example 28

3-(6-Aminopyridin-3-yl)-2-{1-[3-(4-fluorophenoxy)benzyl]-1H-imidazol-4-yl}propionic acid The title compound was prepared in analogy to example 24 and was obtained as bistrifluoroacetate after preparative HPLC.

$R_t$ (method A)=1.09 min. MS (ES+)=433 [M+H]⁺
¹H-NMR (500 MHz, d⁶-DMSO): 2.98 (dd, 1H); 3.13 (dd, 1H); 4.08 (m, 1H); 5.30 (s, 2H); 6.81 (d, 1H); 6.95 (dd, 2H); 7.07 (m, 3H); 7.23 (dd, 2H); 7.40 (dd, 1H); 7.44 (m, 1H); 7.69 (m, 2H); 7.93 (s, br, 2H); 8.87 (s, br, 1H).

Example 29

3-(6-Aminopyridin-3-yl)-2-[1-(2-phenoxybenzyl)-1H-imidazol-4-yl]propionic acid

The title compound was prepared in analogy to example 24 and was obtained as bistrifluoroacetate after preparative HPLC.

$R_t$ (method A)=1.05 min. MS (ES+)=415 [M+H]⁺
¹H-NMR (500 MHz, d⁶-DMSO): 2.97 (dd, 1H); 3.13 (dd, 1H); 4.03 (m, 1H); 5.37 (s, 2H); 6.82 (m, 2H); 6.90 (d, 2H); 7.17 (m, 2H); 7.30 (d, 1H); 7.32-7.43 (m, 4H); 7.69 (m, 2H); 7.92 (s, br, 2H); 8.82 (s, br, 1H).

Example 30

3-(6-Aminopyridin-3-yl)-2-[1-(4-phenoxybenzyl)-1H-imidazol-4-yl]propionic acid

The title compound was prepared in analogy to example 24 and was obtained as bistrifluoroacetate after preparative HPLC.

$R_t$ (method A)=1.08 min. MS (ES+)=415 [M+H]⁺
¹H-NMR (500 MHz, d⁶-DMSO): 2.99 (dd, 1H); 3.13 (dd, 1H); 4.07 (m, 1H); 5.28 (s, 2H); 6.84 (d, 1H); 7.01 (m, 3H); 7.17 (dd, 1H); 7.32 (d, 2H); 7.40 (m, 3H); 7.48 (m, 1H); 7.68 (m, 2H); 7.90 (s, br, 2H); 8.88 (s, br, 1H).

Example 31

3-(6-Aminopyridin-3-yl)-2-(1-prop-2-ynyl-1H-imidazol-4-yl)propionic acid

Example 31a

Dimethyl 2-(6-tert-butoxycarbonylaminopyridin-3-ylmethyl)-2-(1-prop-2-ynyl-1H-imidazol-4-yl)malonate 322 mg (0.99 mmol) of cesium carbonate and sowie 20 µl (0.27 mmol, 80% pure in toluene) of propargyl bromide were successively added to a solution of 100 mg (0.25 mmol) of dimethyl 2-(6-tert-butoxycarbonylaminopyridin-3-ylmethyl)-2-(1H-imidazol-4-yl)malonate (example 12d) in 2 ml of DMF. The mixture was stirred at RT for 3 h and then poured into water and extracted with EA. Purification by chromatography on silica afforded 27 mg of the title compound.

¹H-NMR (400 MHz, CDCl₃): 1.49 (s, 9H); 1.52 (d, 1H); 2.52 (m, 1H); 3.60 (s, 2H); 4.67 (d, 2H); 6.98 (d, 1H); 7.12 (s, 1H); 7.21 (s, 1H); 7.60 (s, 1H); 7.68 (d, 1H).

Example 31b 3-(6-Aminopyridin-3-yl)-2-(1-prop-2-ynyl-1H-imidazol-4-yl)propionic acid A solution of 40 mg (0.09 mmol) of the compound from example 31a in 1.4 ml of 50% concentrated hydrochloric acid was heated at 95° C. for 9 h. Freeze-drying after cooling afforded 21 mg of the title compound as bishydrochloride.

¹H-NMR (500 MHz, d⁶-DMSO): δ=3.11 (dd, 1H); 3.20 (dd, 1H); 3.78 (s, 1H); 4.21 (t, 1H); 5.12 (d, 2H); 6.92 (d, 1H); 7.54 (s, 1H); 7.75 (m, 2H); 8.04 (s, br, 2H); 9.03 (s, 1H).

Example 32

3-(6-Aminopyridin-3-yl)-2-(1-but-2-ynyl-1H-imidazol-4-yl)propionic acid

Example 32a

Ethyl 3-(6-aminopyridin-3-yl)-2-(1-but-2-ynyl-1H-imidazol-4-yl)propionate 11 mg (0.23 mmol, 50%) of sodium hydride were added to a solution of 60 mg (0.23 mmol) of ethyl 3-(6-aminopyridin-3-yl)-2-(1H-imidazol-4-yl)propionate (example 1g) in 0.5 ml of DMF at RT and stirred for 1 h. Then 31 mg (37 µl, 0.23 mmol) of 1-bromo-2-butine were added, and the mixture was stirred at RT for 1 h. 1 ml of water was then added and the mixture was extracted with EA. The organic phase was dried over Na₂SO₄, filtered and concentrated. Chromatography of the residue on silica gel afforded 28 mg of the title compound.

R$_t$ (method A)=0.69 min. MS (ES+)=313 [M+H]⁺

Example 32b 3-(6-Aminopyridin-3-yl)-2-(1-but-2-ynyl-1H-imidazol-4-yl)propionic acid A solution of 25 mg (0.08 mmol) of the compound from example 32a in 2 ml of THF was mixed with 88 µl of 1N NaOH and stirred at RT for 4 h. Then, and again after stirring overnight, 40 µl of NaOH were added. After stirring for a further 24 h, the reaction mixture was neutralized with 2N HCl and freeze-dried. Preparative HPLC afforded 5 mg of the title compound as bistrifluoroacetate.

R$_t$ (method A)=0.23 min. MS (ES+)=285 [M+H]⁺

¹H-NMR (500 MHz, d⁶-DMSO): δ=1.88 (s, 3H); 3.12 (m, 2H); 4.18 (m, 1H); 5.02 (s, 2H); 6.93 (d, 1H); 7.56 (s, 1H); 7.78 (m, 2H); 8.04 (s, br, 2H); 8.97 (s, br, 1H).

The following compounds were prepared in analogy to example 1:

Example 33

3-(6-Aminopyridin-3-yl)-2-[1-(4,4-dimethylcyclohexyl)-1H-imidazol-4-yl]propionic acid as bishydrochloride R$_t$ (method C)=0.93 min. MS (ES+)=343 [M+H]⁺

¹H-NMR (500 MHz, d6-DMSO): δ=0.93 (s, 3H); 1.00 (s, 3H); 1.33 (m, 2H); 1.48 (m, 2H); 1.85 (m, 4H); 3.04 (dd, 1H); 3.20 (dd, 1H); 4.11 (t, 1H); 4.16 (m, 1H); 6.90 (d, 1H); 7.73 (d, 2H); 7.81 (s, 1H); 8.02 (s, 2H, br); 9.14 (s, 1H).

The following compounds were prepared in analogy to example 10:

Examples 34-36

3-(6-Aminopyridin-3-yl)-2-{1-[(benzhydrylmethylcarbamoyl)methyl]-1H-imidazol-4-yl}-propionic acid as bistrifluoroacetate. R$_t$ (method C)=1.18 min MS (ES+)=470[M+H]⁺

3-(6-Aminopyridin-3-yl)-2-[1-({[(4-chlorophenyl)phenylmethyl]carbamoyl}methyl)-1H-imidazol-4-yl]propionic acid as bistrifluoroacetate. R$_t$ (method C)=1.22 min MS (ES+)=490[M+H]⁺ or 3-(6-Aminopyridin-3-yl)-2-[1-({[bis-(4-methoxyphenyl)methyl]carbamoyl}methyl)-1H-imidazol-4-yl]propionic acid as bistrifluoroacetate. R$_t$ (method B)=0.92 min MS (ES+)=516[M+H]⁺.

Example 37

3-(6-Aminopyridin-3-yl)-2-{1-[4-(3-propylureido)phenyl]-1H-imidazol-4-yl}propionic acid

Example 37a

Methyl 3-(6-tert-butoxycarbonylaminopyridin-3-yl)-2-[1-(toluene-4-sulfonyl)-1H-imidazol-4-yl]propionate A solution of 1.00 g (3.39 mmol) of methyl (1-benzenesulfonyl-1H-imidazol-4-yl)acetate (example 1d) in 100 ml of THF was cooled to −78° C. and 3.74 ml (3.74 mmol, 1M in THF) of lithium bis(trimethylsilyl)amide were added in three portions over the course of 3 min. The mixture was stirred at this temperature for 5 min and then 0.65 g (2.26 mmol) of tert-butyl (5-bromomethylpyridin-2-yl)carbamate (example 1b) was added in one portion. The mixture was stirred at −78° C. for 1 h and then allowed to reach RT. The mixture was poured into a mixture of EA and saturated NaHCO₃ solution. After shaking, the organic phase was separated off, dried over Na₂SO₄, filtered and concentrated to dryness. The residue was recrystallized from EA/heptane. The resulting crystals were filtered off with suction, washed with a little EA and heptane and dried. 0.66 g of the title compound was obtained.

R$_t$ (method B)=1.30 min. MS (ES+)=501 [M+H]⁺

Example 37b

Methyl 3-(6-tert-butoxycarbonylaminopyridin-3-yl)-2-(1H-imidazol-4-yl)propionate 0.80 g (5.24 mmol) of 1-hydroxybenzotriazole hydrate was added to a solution of 0.65 g (1.29 mmol) of methyl 3-(6-tert-butoxycarbonylaminopyridin-3-yl)-2-[1-(toluene-4-sulfonyl)-1H-imidazol-4-yl]propionate (example 37a) in 25 ml of methanol, and the mixture was stirred at RT for 2 h. The solvent was evaporated off under reduced pressure, and the residue was purified on silica gel with a mobile phase mixture of CH₂Cl₂ and 10% strength ammonia/methanol.

A second column chromatography on silica gel afforded 341 mg of the title compound.

R$_t$ (method B)=0.78 min. MS (ES+)=347 [M+H]⁺

¹H-NMR (400 MHz, d6-DMSO): δ=1.46 (s, 9H), 3.08 (m, 2H); 3.52 (s, 3H); 3.87 (t, 1H); 6.92 (s, 1H); 6.98 (d, 1H); 7.55 (s, 1H); 7.63 (d, 1H); 7.98 (s, 1H).

Example 37c 3-(6-Aminopyridin-3-yl)-2-{1-[4-(3-propylureido) phenyl]-1H-imidazol-4-yl}propionic acid The title compound was obtained by reacting the compound from Example 37b in analogy to Examples 12e-12g and subsequent elimination in a manner customary in the literature of the protective group in $CH_2Cl_2$/TFA (1:1). Substitution was then carried out as in Example 10c. Preparative HPLC afforded 8 mg of the title compound as bistrifluoroacetate.

$R_t$ (method B)=0.73 min. MS (ES+)=409 [M+H]⁺

¹H-NMR (400 MHz, d6-DMSO): δ=0.88 (t, 3H); 1.45 (dt, 2H); 3.07 (m, 3H); 3.18 (m, 1H); 3.97 (t, 1H); 6.28 (t, 1H); 6.89 (d, 1H); 7.51 (m, 4H); 7.21 (d, 2H); 7.31 (d, 1H); 7.86 (s, 2H, br); 8.19 (s, 1H).

Example 38

3-(6-Aminopyridin-3-yl)-2-{1-[4-toluene-4-sulfonylamino)phenyl]-1H-imidazol-4-yl}-propionic acid Example 38a Methyl 3-(6-tert-butoxycarbonylaminopyridin-3-yl)-2-{1-[bis(4-(toluene-4-sulfonyl)-amino)phenyl]-1H-imidazol-4-yl}propionate A solution of 115 mg (0.26 mmol) of methyl 2-[1-(4-aminophenyl)-1H-imidazol-4-yl]-3-(6-tert-butoxycarbonylaminopyridin-3-yl)propionate (obtained from Example 37b) was dissolved in 20 ml of $CH_3CN$. The solution was cooled to 0° C. and then 60 mg (0.32 mmol) of p-tolulusulfonyl chloride, 73 µl (53 mg, 0.53 mmol) of triethylamine and 0.3 mg (2.6 µmol) of 4-dimethylaminopyridine were added. The mixture was warmed to RT and left to stand overnight. Column chromatography on silica gel afforded 112 mg of the title compound.

$R_t$ (method B)=1.45 min. MS (ES+)=746 [M+H]⁺

Example 38b 3-(6-Aminopyridin-3-yl)-2-{1-[4-(toluene-4-sulfonylamino)phenyl]-1H-imidazol-4-yl}-propionic acid A solution of 109 mg (0.146 mmol) of the compound according to Example 38a in 1 ml of THF was mixed with 190 µl (0.190 mmol) of 1 N aqueous LiOH solution. The mixture was warmed to 40° C. and stirred at this temperature for 2 days. After heating at 60° C. for several hours, the solution was cooled to RT and neutralized with 1 N HCL, and the THF was removed under reduced pressure. The resulting aqueous solution was purified by preparative HPLC, and pure 3-(6-tert-butoxycarbonylaminopyridin-3-yl)-2-{1-[4-(toluene-4-sulfonylamino)phenyl]-1H-imidazol-4-yl}propionic acid was obtained. The compound was dissolved in 1 ml of TFA and stirred at RT. After 30 min, TFA was evaporated off under reduced pressure, and the residue was dissolved in water and lyophilized. 24 mg of the title compound were obtained as bistrifluoroacetate.

$R_t$ (method B)=0.84 min. MS (ES+)=487 [M+H]⁺

¹H-NMR (400 MHz, d6-DMSO): δ=1.22 (s, 3H); 3.02 (dd, 1H); 3.13 (dd, 1H); 3.92 (t, 1H); 6.87 (d, 1H); 7.21 (d, 2H); 7.88 (d, 2H); 7.53 (d, 2H); 7.62 (s, 1H); 7.68 (d, 2H); 7.72 (s, 1H); 7.77 (d, 1H); 7.88 (s, 2H, br); 8.44 (s, 1H, br).

Example 39

3-(6-Aminopyridin-3-yl)-2-{1-[3-(3-propylureido) benzyl]-1H-imidazol-4-yl}propionic acid The title compound was prepared in analogy to Example 38. Only the hydrolysis of the carboxylic ester intermediate was different:

Methyl 3-(6-aminopyridin-3-yl)-2-{1-[3-(3-propylureido) benzyl]-1H-imidazol-4-yl}-propionate (120 mg, 0.275 mmol) were dissolved in THF. An aqueous solution containing LiOH (1 N, 275 µl) and aqueous hydrogen peroxide (30%, 27 µl) were added. The solution was stirred at RT overnight and then at 50° C. for 4 h. The reaction solution was neutralized with aqueous HCL (1 N) and then the solvents were removed. The residue was taken up in a little methanol and filtered through a $C_{18}$ column (500 mg). The methanol was removed and the resulting product was crystallized from diethyl ether (100 mg, 0.237 mmol)

$R_t$ (method C)=0.93 min. MS (ES+)=423 [M+H]⁺

¹H-NMR (500 MHz, d6-DMSO): δ=0.85 (t, 3H), 1.42 (q, 2H); 2.65 (m, 1H), 2.92 (m, 1H); 3.02 (m, 2H); 3.45 (m, 2H); 5.00 (s, 2H); 5.50 (s, 2H); 6.25 (d, 1H); 6.60 (d, 1H); 6.73 (s, 1H); 7.05 (d, 1H); 7.21 (t, 1H); 7.23 (s, 1H); 7.33 (d, 1H); 7.50 (m, 1H); 7.62 (s, 1H); 9.12 (s, 1H).

Example 40

3-(6-Aminopyridin-3-yl)-2-{1-[3-(3-phenethylureido)benzyl]-1H-imidazol-4-yl}propionic acid The compound was prepared in analogy to Example 39.

$R_t$ (method B)=0.86 min. MS (ES+)=485 [M+H]⁺

¹H-NMR (500 MHz, d6-DMSO): δ=2.72 (m, 2H); 2.85 (m, 1H), 2.95 (m, 1H); 3.25 (m, 2H); 3.50 (s, 2H); 4.95 (s, 1H); 5.05 (s, 1H); 5.45 (s, 1H); 5.55 (s, 1H); 6.28 (dd, 1H); 6.65 (t, 1H); 6.92 (s, 1H); 7.08-7.31 (m, 9H); 7.62 (m, 2H); 9.15 (s, 1H).

Example 41

3-(6-Aminopyridin-3-yl)-2-{1-[3-(3-benzylureido) benzyl]-1H-imidazol-4-yl}propionic acid The compound was prepared in analogy to Example 39.

$R_t$ (method B)=0.84 min. MS (ES+)=471 [M+H]⁺

¹H-NMR (500 MHz, d6-DMSO): δ=2.65 (m, 1H); 2.92 (m, 1H), 3.45 (m, 2H); 3.75 (m, 1H); 4.25 (d, 2H); 5.00 (s, 2H); 5.50 (s, 2H); 6.25 (m, 1H); 6.65 (m, 1H); 6.78 (s, 1H); 7.08-7.40 (m, 9H); 7.62 (m, 2H); 9.45 (s, 1H).

Example 42

3-(6-Aminopyridin-3-yl)-2-{1-[3-(3-vinylureido) benzyl]-1H-imidazol-4-yl}propionic acid The compound was prepared in analogy to Example 39.

$R_t$ (method B)=0.60 min. MS (ES+)=407 [M+H]⁺

¹H-NMR (500 MHz, d6-DMSO): δ=2.68 (m, 1H); 2.92 (m, 1H); 3.45 (m, 2H); 3.82 (m, 1H); 4.18 (m, 2H); 5.00 (s,

2H); 5.50 (s, 2H); 6.25 (d, 1H); 6.62-6.77 (m, 3H); 7.09 (m, 1H); 7.25 (m, 2H); 7.45 (m, 1H); 7.62 (m, 2H).

Example 43

3-(2-Aminothiazol-4-yl)-2-{1-[(benzhydrylcarbamoyl)methyl]-1H-imidazol-4-yl}propionic acid The compound was prepared in analogy to Examples 37a-37b and 10b. Elimination of the protective group took place as described.

$R_t$ (method C)=1.13 min. MS (ES+)=462 [M+H]$^+$
$^1$H-NMR (500 MHz, d6-DMSO): δ=2.75 (m, 1H), 3.10 (m, 1H); 3.50 (s, 2H); 3.75 (m, 1H); 3.98 (d, 2H); 6.07 (s, 1H); 6.10 (d, 1H); 6.65 (s, 1H); 7.20-7.35 (m, 9H); 7.39 (s, 1H); 7.40 (t, 1H); 8.78 (d, 1H).

Example 44

3-(2-Aminothiazol-4-yl)-2-[1-({[(4-chlorophenyl)phenylmethyl]carbamoyl}methyl)-1H-imidazol-4-yl]propionic acid The compound was prepared in analogy to Examples 37a-37b and 10b. Elimination of the protective group took place as described.

$R_t$ (method C)=1.26 min. MS (ES+)=496 [M+H]$^+$
$^1$H-NMR (500 MHz, d6-DMSO): δ=2.78 (m, 1H), 3.10 (m, 1H); 3.50 (s, 2H); 3.75 (m, 1H); 3.95 (d, 2H); 6.08 (s, 1H); 6.11 (d, 1H); 6.65 (s, 1H); 7.20-7.41 (m, 9H); 7.60 (t, 1H); 8.85 (d, 1H).

Examples 45 and 46 were prepared in analogy to the above description.

Example 45

3-(6-Aminopyridin-3-yl)-2-{1-[4-(3-tert-butylureido)phenyl]-1H-imidazol-4-yl}propionic acid as bistrifluoroacetate $R_t$ (method B)=0.75 min. MS (ES+)=423 [M+H]$^+$
$^1$H-NMR (400 MHz, d6-DMSO): δ=1.29 (s, 9H); 3.10 (dd, 1H); 3.28 (dd, 1H); 4.09 (t, 1H); 6.72 (d, 2H); 7.28 (d, 1H); 7.33 (d, 2H); 7.56 (d, 1H); 7.85 (s, 1H); 7.92 (s, 1H); 7.99 (s, 1H); 9.03 (s, 1H); 9.28 (s, 1H).

Example 46

3-(6-Aminopyridin-3-yl)-2-{1-[4-(3-benzylureido)phenyl]-1H-imidazol-4-yl}propionic acid as bistrifluoroacetate $R_t$ (method B)=0.81 min. MS (ES+)=457 [M+H]$^+$
$^1$H-NMR (400 MHz, d6-DMSO): δ=3.03 (dd, 1H); 3.18 (dd, 1H); 3.99 (t, 1H); 4.32 (d, 2H); 6.79 (t, 1H); 6.90 (d, 1H); 7.22 (m, 1H); 7.32 (m, 4H); 7.49 (d, 2H); 7.53 (d, 2H); 7.72 (s, 2H); 7.28 (d, 1H); 7.88 (s, 2H, br); 8.71 (s, 1H, br); 8.86 (s, 1H).

Example 47

Ethyl 3-(6-aminopyridin-3-yl)-2-(1-cyclohexyl-1H-imidazol-4-yl)propionate

The title compound was synthesized as hydrochloride in analogy to example 2.

$R_t$ (method C)=0.87 min MS (ES+)=343 [M+H]$^+$
$^1$H-NMR (500 MHz, d$^6$-DMSO): 1.12 (t, 3H), 1.13-1.27 (m, 1H), 1.31-1.41 (m, 2H), 1.61-1.73 (m, 3H), 1.80-1.86 (m, 2H), 1.98-2.05 (m, 2H), 3.12 (dd, 1H), 3.18 (dd, 1H), 4.12 (m, 2H), 4.21-4.27 (m, 2H), 6.93 (d, 1H), 7.72-7.78 (m, 3H), 8.08 (s, 2H), 9.12 (s, 1H).

Pharmacological Examples

The prepared substances were tested for TAFIa inhibition using the Actichrome plasma TAFI activity kit from American Diagnostica (Pr. No. 874). This entailed adding 29 μl of assay buffer (20 mM Hepes, 150 mM NaCl, pH 7.4) and 10 μl of TAFIa (American Diagnostica Pr. No. 874TAFIA; 2.5/ml) to 1 μl of 5 mM DMSO solution of the substance and incubating in a 96 half-well microtiter plate at room temperature for 15 minutes. The enzymic reaction was started by adding 10 μl of TAFIa developer (prediluted 1:2 with water). The time course of the reaction was followed at 420 nm in a microtiter plate reader (SpectraMax plus 384; Molecular Devices) for 15 minutes. The IC$_{50}$ was calculated from the averaged values (duplicate determination) of serial dilutions of the substance with the aid of the Grafit 4 software (Erithacus Software, UK). Table 1 shows the results.

TABLE 1

| Compound from | TAFIa enzyme assay IC$_{50}$ [μM] |
|---|---|
| Example 1 | 0.030 |
| Example 7 | 0.016 |
| Example 8 | 1.13 |
| Example 9 | 0.439 |
| Example 10 | 0.023 |
| Example 12 | 0.015 |
| Example 13 | 0.012 |
| Example 15 | 0.012 |
| Example 16 | 0.038 |
| Example 17 | 0.011 |
| Example 18 | 0.021 |
| Example 25 | 10.51 |
| Example 27 | 1.11 |
| Example 28 | 1.44 |
| Example 31 | 0.87 |
| Example 33 | 0.003 |
| Example 37 | 0.049 |
| Example 38 | 0.050 |

We claim:
1. The compound 3-(6-Aminopyridin-3-yl)-2-(1-cyclohexyl-1H-imidazol-4-yl)propionic acid, which corresponds to the following structure:

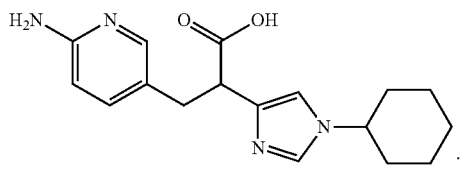 [SMILES: Nc1ccc(CC(C(=O)O)c2cn(C3CCCCC3)cn2)cn1]

* * * * *